United States Patent
Wendeler-Goeggelmann

(10) Patent No.: US 10,549,335 B2
(45) Date of Patent: *Feb. 4, 2020

(54) WIRE MESH AND METHOD FOR IDENTIFYING A SUITABLE WIRE

(71) Applicant: Geobrugg AG, Romanshorn (CH)

(72) Inventor: Corinna Wendeler-Goeggelmann, Herisau (CH)

(73) Assignee: Geobrugg AG, Romanshorn (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/475,868

(22) PCT Filed: Jan. 16, 2018

(86) PCT No.: PCT/EP2018/050974
§ 371 (c)(1),
(2) Date: Jul. 3, 2019

(87) PCT Pub. No.: WO2018/137968
PCT Pub. Date: Aug. 2, 2018

(65) Prior Publication Data
US 2019/0344328 A1 Nov. 14, 2019

(30) Foreign Application Priority Data
Jan. 30, 2017 (DE) .......... 10 2017 101 761

(51) Int. Cl.
*B21F 27/00* (2006.01)
*B21F 27/02* (2006.01)
(Continued)

(52) U.S. Cl.
CPC .......... *B21F 27/005* (2013.01); *B21F 27/02* (2013.01); *G01N 3/20* (2013.01); *E01F 7/045* (2013.01);
(Continued)

(58) Field of Classification Search
CPC ........ B21F 27/02; B21F 27/005; B21F 23/00; B21F 27/14; B21F 9/00; G01N 2203/028;
(Continued)

(56) References Cited

U.S. PATENT DOCUMENTS 1,926,114 A    9/1933  Sellers
2,170,640 A *  8/1939  Kenyon ............... G01N 3/32
                                                    73/810
(Continued)

FOREIGN PATENT DOCUMENTS

CA    2 752 023 A    4/2012
CA    2 752 023 C    4/2012
(Continued)

OTHER PUBLICATIONS

Search Report dated May 22, 2017 issued in corresponding DE patent application No. 10 2017 101 761.5 (and English translation).
(Continued)

*Primary Examiner* — Robert H Muromoto, Jr.
(74) *Attorney, Agent, or Firm* — Posz Law Group, PLC

(57) ABSTRACT

A wire netting, in particular a safety net, includes a plurality of helices which are braided with one another and at least one of which is manufactured of at least one single wire, a wire bundle, a wire strand, a wire rope and/or another longitudinal element with at least one wire, in particular made of a high-tensile steel. The wire is bendable in a reverse bend test in opposite directions, by at least 90° respectively, about at least one bending cylinder having a diameter of maximally 2 d, at least M times without breaking, wherein M may be determined (by rounding down if applicable) to be $C \cdot R^{-0.5} \cdot d^{-0.5}$ and wherein a diameter d of the wire is given in mm, R is a tensile strength of the wire in N mm$^{-2}$ and C is a factor of at least 400 N$^{0.5}$ mm$^{0.5}$.

9 Claims, 13 Drawing Sheets

Figure 1:
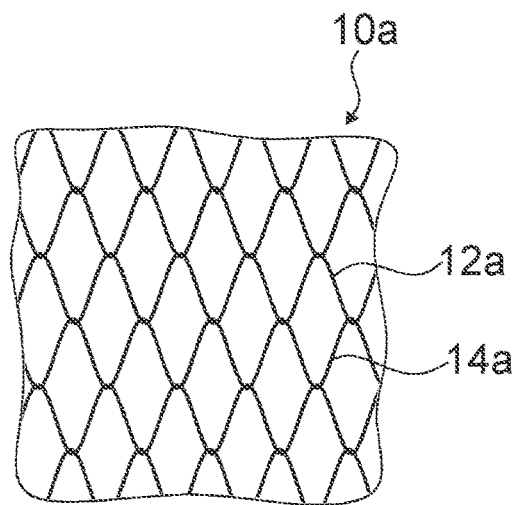

(51) Int. Cl.
*G01N 3/20* (2006.01)
*E01F 7/04* (2006.01)

(52) U.S. Cl.
CPC ............... *G01N 2203/0023* (2013.01); *G01N 2203/028* (2013.01)

(58) Field of Classification Search
CPC ... G01N 2203/0005; G01N 2203/0023; G01N 2203/0073; G01N 3/32; G01N 3/20; G01N 2203/0016; G01N 2203/0278; E02B 3/124; C21D 2201/01; C21D 2201/02; D04C 1/06; D07B 1/066; D10B 2101/20; D10B 2507/02; Y10T 428/294; Y10T 29/49004; Y10T 29/5187
See application file for complete search history.

(56) References Cited

U.S. PATENT DOCUMENTS

| | | | |
|---|---|---|---|
| 3,643,497 A * | 2/1972 | LeCompte | B21F 9/00 73/794 |
| 4,049,224 A | 9/1977 | Wener et al. | |
| 4,737,392 A * | 4/1988 | Dambre | B60C 9/0007 152/451 |
| 5,590,755 A | 1/1997 | Daringer et al. | |
| 6,279,858 B1 | 8/2001 | Eicher | |
| 6,591,692 B2 * | 7/2003 | Kawakita | G01N 3/20 73/810 |
| 8,678,709 B2 * | 3/2014 | Utz | E01F 7/04 256/12.5 |
| 9,333,553 B2 * | 5/2016 | Wartmann | B21F 27/04 |
| 9,452,467 B2 * | 9/2016 | Atz | A01K 75/00 |
| 10,058,909 B2 * | 8/2018 | Wendeler-Goeggelmann | B21F 27/04 |
| 10,145,045 B2 * | 12/2018 | Wendeler-Goeggelmann | B21F 27/04 |
| 2001/0024124 A1 * | 9/2001 | Kawakita | G01N 3/20 324/503 |
| 2002/0059834 A1 * | 5/2002 | Onoue | G01N 3/32 73/812 |
| 2003/0066185 A1 * | 4/2003 | Akizuki | B60R 16/0207 29/749 |
| 2005/0013565 A1 * | 1/2005 | Mohler | G02B 6/4422 385/113 |
| 2011/0054351 A1 * | 3/2011 | Fox | A61L 27/06 600/585 |
| 2014/0370285 A1 * | 12/2014 | Fox | A61L 27/06 428/379 |
| 2015/0041599 A1 | 2/2015 | Wartmann | |
| 2015/0213913 A1 | 7/2015 | Yoshida et al. | |

FOREIGN PATENT DOCUMENTS

| | | |
|---|---|---|
| CH | 703 929 B1 | 4/2012 |
| CH | 706 178 A2 | 8/2013 |
| CN | 102444113 A | 5/2012 |
| CN | 202804036 U | 3/2013 |
| CN | 103317067 A | 9/2013 |
| CN | 205134341 U | 4/2016 |
| CN | 205743618 U | 11/2016 |
| DE | 20 36 468 A1 | 1/1972 |
| DE | 30 28 019 A1 | 2/1981 |
| EP | 0 144 811 A2 | 6/1985 |
| RU | 2 229 561 C2 | 5/2004 |
| WO | 99/43894 A1 | 9/1999 |

OTHER PUBLICATIONS

Office Action dated Oct. 26, 2017 issued in corresponding DE patent application No. 10 2017 101 761.5 (and English translation).
Notice of Allowance dated Mar. 8, 2018 issued in corresponding DE patent application No. 10 2017 101 761.5 (and English translation).
International Search Report dated May 15, 2018 issued in corresponding International Patent Application No. PCT/EP2018/050974.
International Preliminary Report on Patentability dated Jul. 30, 2019 issued in corresponding International Patent Application No. PCT/EP2018/050974.
Canadian Office Action dated Sep. 3, 2019 issued in corresponding CA patent application No. 3, 051, 935.
Chinese Office Action dated Nov. 6, 2019 issued in corresponding CN patent application No. 201880008832.4 (English summary attached).

* cited by examiner

WIRE MESH AND METHOD FOR IDENTIFYING A SUITABLE WIRE

CROSS REFERENCE TO RELATED APPLICATIONS

This application is a U.S. national stage application of PCT/EP2018/050974 filed on Jan. 16, 2018, which is based on German Patent Application No. 10 2017 101 761.5 filed on Jan. 30, 2017, the contents of which are incorporated herein by reference.

STATE OF THE ART

The invention relates to a wire netting and to a method for an identification of a suitable wire that is made of a high-tensile steel according to the claims.

From the state of the art wire nettings are known which are made of high-tensile steel wire netting. High-tensile steel wire is comparably prone to breaking when bent, which may lead, despite of a great tensile strength, to a reduced load-bearing capacity of the wire netting, resulting in a high amount of discard in manufacturing.

The objective of the invention is in particular to provide a generic wire netting with advantageous characteristics regarding load-bearing capacity. The objective is achieved, according to the invention, by the recited features of the independent claims while advantageous implementations and further developments of the invention may be gathered from the dependent claims.

Advantages of the Invention

In one aspect of the invention, which may be considered on its own or in combination with at least one aspect, in particular in combination with one aspect, in particular in combination with any number of the remaining aspects of the invention, a wire netting, in particular a safety net, is proposed, with a plurality of helices which are braided with one another, and at least one of which is manufactured of at least one single wire, of a wire bundle, of a wire strand, of a wire rope and/or of another longitudinal element with at least one wire and which comprises at least one first leg, at least one second leg and at least one bending region connecting the first leg and the second leg to one another, wherein, in a front view perpendicularly to a main extension plane of the helix, the first leg extends featuring at least one first gradient angle with respect to a longitudinal direction of the helix, wherein, in a transverse view in parallel to the main extension plane of the helix and perpendicularly to the longitudinal direction of the helix, the bending region extends at least section-wise with a second gradient angle with respect to the longitudinal direction of the helix, wherein the second gradient angle differs from the first gradient angle, in particular beyond a range of manufacturing tolerances. In this way a high load-bearing capacity is advantageously achievable. Moreover a high degree of safety is achievable. It is in particular possible to make a wire netting with a high degree of strength, in particular tensile strength, available. Advantageously a geometry of helices and/or meshes of a netting is adaptable to a strain that is to be expected. Beyond this a load-bearing capacity of intersection points and/or node points in a netting may be increased. Advantageously different regions of a helix of a wire netting may be optimized individually and load-specifically. This moreover advantageously allows providing a wire netting with a high degree of rigidity, in particular transversely to the netting and/or along the netting. Furthermore mechanical properties of a wire netting may be adapted flexibly and/or according to requirements.

The invention moreover concerns a method for manufacturing a helix for a wire netting, in particular for a safety net, in particular a method for producing a wire netting, in particular a safety net, wherein the helix is manufactured of at least one single wire, of a wire bundle, of a wire strand, of a wire rope and/or of another longitudinal element with at least one wire, and wherein at least one first leg, at least one second leg and at least one bending region of the helix connecting the first leg and the second leg to one another are produced by way of bending, as a result of which, in a first view perpendicularly to the main extension plane of the helix, the first leg and/or the second leg extends at least with a first gradient angle with respect to a longitudinal direction of the helix. It is proposed that the helix is produced by bending in such a way that, in a second view in parallel to the main extension plane of the helix and perpendicularly to the longitudinal direction of the helix, the bending region extends at least section-wise with a second gradient angle with respect to the longitudinal direction of the helix that differs from the first gradient angle. In this way a high load-bearing capacity is advantageously achievable. Moreover a high degree of safety is achievable. It is in particular possible to make a wire netting with a high degree of strength, in particular tensile strength, available. Advantageously a geometry of helices and/or meshes of a netting is adaptable to a strain that is to be expected. Beyond this a load-bearing capacity of intersection points and/or node points in a netting may be increased. Advantageously different regions of a helix of a wire netting may be optimized individually and load-specifically. This moreover advantageously allows providing a wire netting with a high degree of rigidity, in particular transversely to the netting and/or along the netting. Furthermore mechanical properties of a wire netting may be adapted flexibly and/or according to requirements.

In a further aspect of the invention, which may be considered on its own or in combination with at least one aspect, in particular in combination with one aspect, in particular in combination with any number of the remaining aspects of the invention, a wire netting, in particular a safety net, is proposed, with a plurality of helices which are braided with one another and at least one of which is manufactured of at least one single wire, of a wire bundle, of a wire strand, of a wire rope and/or of another longitudinal element with at least one wire and which comprises at least one first leg, at least one second leg and at least one bending region wherein, in a longitudinal view in parallel to a longitudinal direction of the helix, the bending region comprises at least one bending zone with a bending curvature as well as at least one first transition zone which is connected to the first leg and has a first transition curvature that differs from the bending curvature. This allows achieving advantageous characteristics regarding a load-bearing capacity. Moreover a high degree of safety is achievable. It is in particular possible to make a wire netting with a high degree of strength, in particular tensile strength, available. Advantageously a geometry of helices and/or meshes of a netting is adaptable to a strain that is to be expected. Advantageously different regions of a helix of a wire netting may be optimized individually and load-specifically. This moreover advantageously allows providing a wire netting with a high degree of rigidity, in particular transversely to the netting and/or along the netting. Furthermore mechanical properties of a wire netting may be adapted flexibly and/or according to requirements. Beyond this a behavior of a bending region in case of a load is optimizable. Moreover a large parameter space may be rendered available regarding a bending region geometry.

The invention further concerns a method for producing a helix for a wire netting, in particular a safety net, in particular a method for producing a wire netting, in particular a safety net, wherein the helix is manufactured of at least one single wire, of a wire bundle, of a wire strand, of a wire rope and/or of another longitudinal element with at least one wire, and wherein at least one first leg, at least one second leg and at least one bending region of the helix connecting the first leg and the second leg to one another are produced by way of bending. It is proposed that the helix is produced by bending such, in a longitudinal view in parallel to a longitudinal direction of the helix, the bending region comprises at least one bending zone with a bending curvature and comprises at least one first transition zone that is connected to the first leg and has a first transition curvature differing from the bending curvature. This allows achieving advantageous characteristics regarding a load-bearing capacity. Moreover a high degree of safety is achievable. It is in particular possible to make a wire netting with a high degree of strength, in particular tensile strength, available. Advantageously, a geometry of helices and/or meshes of a netting is adaptable to a strain that is to be expected. Advantageously different regions of a helix of a wire netting may be optimized individually and load-specifically. This moreover advantageously allows providing a wire netting with a high degree of hardness, in particular transversely to the netting and/or along the netting. Furthermore mechanical properties of a wire netting may be adapted flexibly and/or according to requirements. Beyond this a behavior of a bending region in case of a load is optimizable. Moreover a large parameter space may be rendered available regarding a bending region geometry.

In a further aspect of the invention, which may be considered on its own or in combination with at least one aspect, in particular in combination with one aspect, in particular in combination with any number of the remaining aspects of the invention, a wire netting, in particular a safety net, is proposed, with a plurality of helices which are braided with one another and at least one of which is manufactured of at least one single wire, of a wire bundle, of a wire strand, of a wire rope and/or of another longitudinal element with at least one wire, which is in particular made of a high-tensile steel wherein, in a reverse bend test, the wire is bendable in opposite directions, by at least 90° respectively, about at least one bending cylinder having a diameter of maximally 2 d, at least M times without breaking, wherein M may be determined (by rounding down if applicable) to be $C \cdot R^{-0.5} \cdot d^{-0.5}$ and wherein a diameter d of the wire is given in mm, R is a tensile strength of the wire in N mm$^{-2}$ and C is a factor of at least 400 N$^{0.5}$ mm$^{0.5}$. This allows achieving advantageous characteristics regarding processability and/or manufacturability. Moreover a robust wire netting may be made available. It is furthermore possible to achieve a high degree of safety. In particular, a wire netting may be rendered available featuring a high strength, in particular tensile strength. Advantageously a wire netting with balanced characteristics regarding hardness and tensile strength may be made available. Furthermore, a wire breakage is advantageously avoidable in a production of wire nettings. In particular, in a production of wire nettings test runs may advantageously be dispensed with, at least to a large extent. Beyond this it is possible to simply and/or quickly and/or reliably identify wires suitable for a wire netting with a high load-bearing capacity. In particular, a selection method for a suitable wire may be provided which is significantly more rigorous and/or more load-specific as compared to a reverse bend test according to ISO 7801.

The invention moreover concerns a method for identifying a suitable wire, in particular a wire made of a high-tensile steel, for a wire netting, in particular for a safety net, with a plurality of helices which are braided with one another, wherein at least one of the helices is to be manufactured of at least one single wire, a wire bundle, a wire strand, a wire rope and/or another longitudinal element with a suitable wire. It is proposed that the wire is identified as suitable if in a reverse bend test a test piece of the wire is bendable in opposite directions, by at least 90° respectively, about a bending cylinder having a diameter of maximally 2 d, at least M times without breaking, wherein M may be determined (by rounding down if applicable) to be $C \cdot R^{-0.5} \cdot d^{-0.5}$ and wherein a diameter d of the wire is given in mm, R is a tensile strength of the wire in N mm$^{-2}$ and C is a factor of at least 400 N$^{0.5}$ mm$^{0.5}$. This allows achieving advantageous properties regarding a load-bearing capacity. It is furthermore possible to achieve a high degree of safety. In particular, a wire netting may be rendered available featuring a high strength, in particular tensile strength. Advantageously a wire netting with balanced characteristics regarding rigidity and tensile strength may be made available. Moreover wire breakage is advantageously avoidable in a production of wire nettings. In particular, in a production of wire nettings test runs may advantageously be dispensed with, at least to a large extent. Beyond this it is possible to identify wires suitable for a wire netting with a high load-bearing capacity simply and/or quickly and/or reliably.

In another aspect of the invention, which may be considered on its own or in combination with at least one aspect, in particular in combination with one aspect, in particular in combination with any number of the remaining aspects of the invention, a wire netting, in particular a safety net, is proposed, with a plurality of helices which are braided with one another and at least one of which is manufactured of at least one single wire, of a wire bundle, of a wire strand, of a wire rope and/or of another longitudinal element with at least one wire which is made of a high-tensile steel and which comprises a plurality of legs, a plurality of bending regions respectively connecting two legs, and which has a transverse extension along a frontal direction, perpendicularly to a main extension plane of the helix, wherein, in a press test between parallel plates comprising a pressing by moving the plates along a press path in parallel to the frontal direction, a test piece of the helix, taken from the helix and comprising at least five legs and at least four bending regions, shows a spring characteristic curve which has in a press path force diagram, starting from a start of the press path, a first partial characteristic curve running at least approximately linearly or running linearly and having a first gradient. The press path force diagram is herein in particular a path-force-diagram. This allows achieving advantageous characteristics regarding a load-bearing capacity. Moreover a high degree of safety is achievable. It is in particular possible to provide a wire netting with a high strength, in particular a high tensile strength. Advantageously a wire netting may be rendered available with balanced properties regarding a hardness as well as a tensile strength. Moreover a wire netting with a high level of robustness regarding forces acting transversely to the netting, in particular forces resulting from impacting objects, may be rendered available. Beyond this a suitability of a netting may be determined simply and/or quickly and/or reliably.

In a further aspect of the invention, which may be considered on its own or in combination with at least one aspect, in particular in combination with one aspect, in particular in combination with any number of the remaining aspects of the invention, a bending device for producing a wire netting, in particular a safety net, is proposed, which comprises a plurality of helices which are braided with one another and at least one of which is manufactured of at least one helix blank, namely a single wire, a wire bundle, a wire strand, a wire rope and/or another longitudinal element with at least one wire, with a bending unit comprising at least one bending mandrel and at least one bending table that is configured for bending the helix blank about the bending mandrel and is supported in a manner entirely circulating about the bending mandrel, with a feed unit configured for conveying the helix blank along a feed axis in a feed direction, and with a geometry adjusting unit which is configured for adjusting a geometry of the helix. In this way advantageous characteristics are achievable regarding a production. In particular, regarding a production of a wire netting a large parameter space may be made available. Moreover, a geometry of helices and/or meshes of a wire netting may be adapted variably and/or according to requirements. Beyond this, a quick and/or reliable production may be facilitated. It is furthermore possible to make bending device available that is adjustable flexibly and/or comprehensively. In addition a high production throughput is achievable. Moreover, in a bending of a helix of a wire netting, slowing down of moving parts, which in particular means a high time and/or energy input, may be dispensed with to a large extent. A low-maintenance bending unit may be provided and/or downtimes, e.g. due to maintenance, may be reduced.

"Configured" is in particular to mean specifically programmed, designed and/or equipped. By an object being configured for a certain function is in particular to be understood that the object fulfills and/or implements said certain function in at least one application state and/or operating state. By a method being "configured" for a purpose is in particular to be understood that the method comprises at least one method step that is specifically directed to the purpose and/or that the method is directly focused on the purpose and/or that the method serves for fulfilling the purpose and is at least partly optimized therefor. By a method step being "configured" for a purpose is in particular to be understood that the method step is specifically aimed at the purpose and/or that the method step is directly aimed at the purpose and/or that the method step serves for fulfilling the purpose and is at least partly optimized for said fulfillment.

Advantageously it is possible to provide a wire netting that has a good load-bearing capacity and/or is producible in such a way that it is adapted to a requirement profile, and/or to provide a method for its production that is flexibly adaptable and/or reliable. Advantageously mechanical properties of bending regions and/or connection points and/or legs and/or netting helices may be optimized and/or adapted independently as well as synergistically. Beyond this, a method for quality control is provided that is easily applicable and/or yields reliable results.

In particular, the helix is manufactured from a longitudinal element, namely a single wire, a wire bundle, a wire strand, a wire rope and/or another longitudinal element comprising at least the wire. By a "wire" is in particular, in this context, a body to be understood which is elongate and/or thin and/or at bendable at least machine-wise and/or flexible. Advantageously the wire has along its longitudinal direction an at least substantially constant cross section, which is in particular circle-shaped or elliptic. Especially advantageously the wire is embodied as a round wire. It is however also conceivable that the wire is embodied, at least section-wise or completely, as a flat wire, a four-edge wire, a polygonal wire and/or a profile wire. The wire may be implemented, for example, at least partly or completely of metal, in particular a metal alloy, and/or of an organic and/or inorganic synthetic material and/or of a composite material and/or of an inorganic non-metallic material and/or of a ceramic material. It is conceivable, for example, that the wire is implemented as a polymer wire or as a synthetic wire. In particular, the wire may be embodied as a composite wire, e.g. as a metal-organic composite wire and/or as a metal-inorganic composite wire and/or as a metal-polymer composite wire and/or as a metal-metal composite wire or the like. It is in particular conceivable that the wire comprises at least two different materials which are in particular arranged with respect to one another following a composite geometry and/or are at least partly mixed up with each other. Advantageously the wire is embodied as a metal wire, in particular as a steel wire, in particular as a stainless steel wire. If the helix comprises a plurality of wires, these are preferably identical. It is however also conceivable that the helix comprises a plurality of wires which differ from one another regarding their materials and/or diameters and/or cross sections. Preferentially the wire has an in particular corrosion-resistant coating and/or cladding, e.g. a zinc coating and/or an aluminum-zinc coating and/or a plastic coating and/or a PET coating and/or a metal oxide coating and/or a ceramic coating or the like.

Advantageously the transverse extension of the helix is greater, in particular considerably greater than a diameter of the wire and/or than a diameter of the longitudinal element which the helix is made of. Depending on an application and in particular depending on a desired load-bearing capacity and/or depending on desired spring characteristic curves of the wire netting, in particular in a frontal direction, the transverse extension may be, for example, twice or three times or five times or ten times or twenty times as great as the diameter of the longitudinal element, wherein values in between or smaller values or greater values are also conceivable. Likewise, depending on a utilization, the wire may have a diameter of, for example, approximately 1 mm, approximately 2 mm, approximately 3 mm, approximately 4 mm, approximately 5 mm, approximately 6 mm, approximately 7 mm or even more or even less or a diameter having a value in between. Larger diameters, in particular considerably larger diameters are also conceivable if the longitudinal element comprises a plurality of components, in particular a plurality of wires, e.g. in a case of a wire rope, or a wire strand, or a wire bundle, or the like.

In particular, the wire netting is implemented as a slope protection, as a safety fence, as a catch fence, as a rock-fall protection net, as a barrier fence, as a fish-farming net, as a net protecting from predatory animals, as an enclosure fence, as a tunnel safeguarding, as a landslide protection, as a motor sport protection fence, as a road fence, as an avalanche protection or the like. In particular due to its high strength and/or load-bearing capacity, applications as a covering and/or as a cladding, e.g. of power plants, factory buildings, residential or other buildings, as an explosion protection, as a bullet protection, as a screening against flying objects, as a catch net, as a ram protection or the like are also conceivable. The wire netting may, for example, be laid out and/or arranged and/or mounted horizontally or vertically or obliquely, in particular with respect to a ground.

In particular, the wire netting is embodied planar. Advantageously the wire netting is structured regularly and/or in at least one direction periodically. Preferentially the wire netting is capable of being rolled up and/or rolled out, in particular about an axis which extends in parallel to the main extension direction of the helix. In particular, a roll that is rolled up of the wire netting may be rolled out in a direction that is perpendicular to the main extension direction of the helix.

The helix is preferably embodied spiral-shaped. In particular, the helix is embodied as a flattened spiral. Preferably a plurality of bending regions and a plurality of legs implement the helix, wherein advantageously bending regions are respectively connected to legs directly. Advantageously a transverse extension is considerably smaller than a length of the first leg. In particular, the helix advantageously has along its contour an at least substantially constant diameter and/or cross section, or a constant diameter and/or cross section. Especially preferentially the helix comprises a plurality of legs, which are advantageously implemented at least substantially identically or identically. Advantageously the helix comprises a plurality of bending regions, which respectively connect two neighboring legs and which are preferably embodied at least substantially identically or identically. Preferably the helix is implemented of one single longitudinal element, in particular only of the longitudinal element, e.g. of the wire or of a wire strand or of a wire rope or of a wire bundle or the like. By "at least substantially identical" objects is in particular to be understood, in this context, that the objects are structured in such a way that they are respectively capable of fulfilling a shared function and differ from one another structurally, except for manufacturing tolerances, if at all, by individual elements which are not essential for the shared function. Preferably "at least substantially identical" is to mean identical except for manufacturing tolerances and/or in the scope of manufacture-technological possibilities. An "at least substantially constant value" is in particular to mean, in this context, a value varying by maximally 20%, advantageously by no more than 15%, especially advantageously by maximally 10%, preferably by no more than 5%, preferentially by maximally 3% and particularly preferably by maximally 2% or even maximally 1%. By an object having an "at least substantially constant cross section" is in particular to be understood that, for any first cross section of the object along at least one direction and any second cross section of the object along the direction, a minimum surface area of a difference surface resulting from one of the cross sections being laid over the other one is maximally 20%, advantageously maximally 10% and especially advantageously no more than 5% of the surface area of the larger one of the two cross sections.

Preferentially the longitudinal direction of the helix is arranged at least substantially parallel or parallel to a main extension direction of the helix. Preferentially the helix has a longitudinal axis extending in parallel to the longitudinal direction of the helix. Preferably the main extension plane of the helix is arranged at least substantially parallel to a main extension plane of the wire netting, at least in a state when the wire netting is laid out and/or rolled out in a planar fashion, which may in particular differ from an installed state of the wire netting. By a "main extension direction" of an object is herein in particular a direction to be understood which extends in parallel to a largest edge of a smallest imaginary rectangular cuboid which just still encloses the object. By "at least substantially parallel" is here in particular an orientation of a direction with respect to a reference direction, in particular in a plane, to be understood, wherein the direction deviates from the reference direction in particular by less than 8°, advantageously by less than 5° and especially advantageously by less than 2°. By a "main extension plane" of an object is in particular a plane to be understood which is parallel to a largest side surface of a smallest imaginary rectangular cuboid just still completely enclosing the object, and which in particular extends through the center of the rectangular cuboid.

The wire netting preferably comprises a plurality of or several helices, in particular identically implemented helices. It is also conceivable that the wire netting is implemented of a plurality of different helices. Advantageously the helices are interconnected. In particular, neighboring helices are arranged in such a way that their longitudinal directions extend in parallel. Preferably respectively one helix is braided and/or twisted in with two neighboring helices. In particular, the wire netting is producible by a helix being twisted into a pre-netting, a further helix being twisted into said twisted-in helix, another helix being then twisted into said further twisted-in helix, and so forth. Advantageously neighboring helices are connected via their bending regions. Especially advantageously respectively two bending regions of different helices connected to each other, in particular hooked in with one another. In particular, the helices of the wire netting have the same direction of rotation. Advantageously respectively two helices are knotted with one another, in particular at a respective first one of their ends and/or at a respective second one of their ends situated opposite the first ends.

Preferentially the wire netting comprises at least one mesh. Especially preferentially the mesh is delimited by four legs, respectively two of which belong to the same helix. Advantageously the helix delimits the mesh from at least one side, in particular from two sides. In particular, the mesh is quadrangular, in particular rhomboid-shaped. Advantageously the mesh is symmetrical to a symmetry axis extending in parallel to the longitudinal direction of the helix and/or symmetrical to a symmetry axis extending perpendicularly to the longitudinal direction of the helix. Preferably the mesh has a first interior angle. Especially preferentially the first interior angle has an absolute value that is twice as large as the absolute value of the first gradient angle. In particular, the first interior angle is composed of two gradient angles of neighboring helices. Advantageously the longitudinal axis of the helix is an angle bisector of the first angle. Preferentially the mesh features a second interior angle that is arranged adjacently to the first interior angle. In particular, a sum of half the absolute value of the second interior angle and an absolute value of the gradient angle is at least substantially or precisely 90°. Advantageously an angle bisector of the second interior angle is oriented perpendicularly to the longitudinal axis of the helix. Especially advantageously the mesh has a third interior angle that is arranged opposite the first interior angle. In particular, the absolute value of the third interior angle is identical to the absolute value of the first interior angle. Advantageously the mesh has a fourth interior angle that is arranged opposite the second interior angle. In particular, the absolute value of the fourth interior angle is identical to the absolute value of the second interior angle. Advantageously the wire netting comprises a plurality of meshes, which are in particular at least substantially identical or identical. Particularly advantageously respectively two neighboring helices implement a plurality of meshes. Preferably the first leg and the second leg form the mesh together with a further first leg and a further second leg of a further helix that is arranged adjacently to the helix. "At least substantially" is in particular to mean, in this context, that a deviation from a given value is in particular less than 15%, preferably less than 10% and especially preferentially less than 5% of the given value.

The first gradient angle is advantageously an angle included by a longitudinal axis of the first leg and the longitudinal axis of the helix, in particular in a front view. Especially advantageously the second gradient angle is an angle included by a main extension direction of the bending region and the longitudinal axis of the helix, in particular in a transverse view.

The bending zone in particular comprises at least 25%, advantageously at least 50%, especially advantageously no less than 75% and preferably at least 85% of the bending region.

Preferentially the first leg is connected to the bending region, in particular to the first transition zone, integrally. Especially preferentially the second leg is connected to the bending region integrally. Advantageously the first transition zone is connected to the bending zone integrally. Particularly preferably the helix is embodied in a one-part implementation. In particular, a main extension plane of the bending region differs from a main extension plane of the first transition zone. It is however also conceivable that the bending region and the first transition zone share a main extension plane. "Integrally" is in particular to mean connected at least by substance-to-substance bond, e.g. by a welding process, an adhesive-bonding process, an injection-molding process and/or another process that is deemed expedient by someone skilled in the art, and/or advantageously formed in one piece, e.g. by manufacturing from one cast and/or by manufacturing in a one-component or multi-component injection molding procedure, and advantageously from a single blank. If the helix is implemented of a longitudinal element with a plurality of components, e.g. a strand and/or a wire rope and/or a wire bundle, "integrally" is in particular to mean, in this context, that component wires and/or other components of the longitudinal element have no interruption along a contour of the helix. The helix is in particular manufactured of a single longitudinal element or of a single longitudinal-element blank.

In the reverse bend test the wire is preferably bent around two opposite-situated, identically implemented bending cylinders. Advantageously the bending cylinders are configured to execute the reverse bend test without deformation and/or non-destructively.

Advantageously the test piece of the helix is embodied in a one-part implementation. The test piece of the helix preferably has exactly four bending regions. Particularly preferably the test piece of the helix has exactly five legs. In particular, the parallel plates are configured to carry out the press test deformation-free and/or non-destructively. In particular, in pressing a first plate of the two parallel plates is moved towards a second plate of the two parallel plates along the press path. In particular, in pressing the first plate moves with a speed of no less than 10 µm s$^{-1}$, advantageously at least 50 µm s$^{-1}$, especially advantageously no less than 100 µm s$^{-1}$, preferably approximately 117 µm s$^{-1}$ with respect to the second plate. In particular, the test piece of the helix is irreversibly deformed in the press test. "Extending at least approximately linearly" is in particular to mean, in this context, extending free of jumps and/or with an at least substantially constant gradient.

The feed unit advantageously comprises at least one feed element, which is in particular driven and which in feeding exerts a feed force onto the helix blank. The feed element is preferably embodied as a feed roll. Especially advanta-geously the feed unit comprises a plurality of feed elements, wherein in particular at least one of the feed elements, advantageously several, especially advantageously all of the feed elements are driven, and wherein in the forward-feeding the helix blank is conveyed between the feed elements.

In particular, the geometry adjusting unit is configured to adjust a curvature of the bending region, in particular of the bending zone and/or of the first transition zone, and/or a length of the first leg and/or a length of the second leg and/or the transverse extension of the helix and/or the first gradient angle and/or the second gradient angle and/or a geometry of the mesh. Advantageously the bending device is configured to produce the helix according to the invention. In particular, the bending device is configured to produce the wire netting according to the invention.

The bending device advantageously comprises a braiding unit, which is configured to braid the helix into a pre-netting, in particular a pre-netting implemented of a plurality of helices which are at least substantially identical or identical to the helix.

Preferably the bending mandrel is supported rotatably about a longitudinal axis of the bending mandrel. In particular, the bending mandrel is driven. Advantageously the bending device, in particular the bending unit, comprises at least one drive unit for the bending mandrel, which rotates the bending mandrel about its longitudinal axis. Preferably the bending device, in particular the bending unit, comprises at least one drive unit for the bending table, which is configured to drive the bending table about the bending mandrel in circulating fashion. The bending device preferably comprises a single drive unit, which is connected to driven and/or moved components of the bending device via suitable belts, wheels, transmissions, etc. and/or is configured to drive said driven and/or moved components.

In a further implementation of the invention it is proposed that the wire is produced at least partially, in particular completely, irrespective from a coating, of a high-tensile steel. The wire is preferably a high-tensile steel wire. For example, the high-tensile steel may be spring steel and/or wire steel and/or a steel suitable for wire ropes. In particular, the wire has a tensile strength of at least 800 N mm$^{-2}$ advantageously no less than 1000 N mm$^{-2}$, especially advantageously at least 1200 N mm$^{-2}$, preferably no less than 1400 N mm$^{-2}$ and particularly preferably at least 1600 N mm$^{-2}$, in particular a tensile strength of approximately 1770 N mm$^{-2}$ or approximately 1960 N mm$^{-2}$. It is also conceivable that the wire has an even higher tensile strength, e.g. a tensile strength of at least 2000 N mm$^{-2}$, or of no less than 2200 N mm$^{-2}$, or even at least 2400 N mm$^{-2}$. This allows achieving a high load-bearing capacity, in particular a high tensile strength and/or a high rigidity transversely to the netting. Moreover advantageous bending characteristics are achievable.

In an advantageous implementation of the invention it is proposed that the second gradient angle differs from the first gradient angle by at least 2.5°, preferably by no less than 5°, advantageously by at least 10°, especially advantageously by no less than 15°, preferably by no less than 20°, particularly preferably by at least 25°. This allows application-specific optimizing of a geometry of connecting points.

In a particularly advantageous implementation of the invention it is proposed that the second gradient angle has a value between 25° and 65°, advantageously between 40° and 50°. In particular, the second gradient angle is at least 25°, advantageously no less than 30°, especially advantageously at least 35° and preferably no less than 40°, and/or maximally 65°, advantageously no more than 60°, especially advantageously no more than 55° and preferably maximally 50°. In particular, the second gradient angle is at least substantially 45°, in particular precisely 45°. Particularly preferably the bending regions of the helix of the netting feature a second gradient angle of approximately 45°. This allows achieving a geometry of a bending region which has a high load-bearing capacity and/or is advantageously connectable to a further bending region.

Beyond this it is proposed that in a transverse view the bending region, in particular the bending zone, follows at least section-wise an at least approximately straight contour, in particular a straight contour. "At least approximately straight" is in particular to mean, in this context, straight, in particular linear, in the range of manufacturing tolerances. Preferably, in the transverse view a section of the bending region follows the approximately straight contour or straight contour, said section comprising at least 50%, advantageously at least 75% and especially advantageously at least 85% of the bending region. Advantageously the bending region is in the section, in particular in a proximity of the bending region, curved in a plane which is arranged in parallel to the approximately straight contour of the bending region. Preferably, in the front view the approximately straight contour extends at least substantially parallel or parallel to the longitudinal direction of the helix. This allows providing a bending region having a high tensile strength and/or a high flexural rigidity. Furthermore, in this way a geometry may be rendered available which is advantageous regarding a connection of bending regions of different helices.

It is also proposed that, in the transverse view, the helix follows at least section-wise a stepped course, in particular an obliquely-stepped course. Preferably, in the transverse view the first leg, the bending region and the second leg implement the stepped course, wherein the bending region or at least the approximately straight contour of the bending region includes an angle with the first leg and/or the second leg corresponds to the second gradient angle.

A high rigidity of a wire netting transversely to its surface is achievable if the first leg and/or the second leg at least section-wise follows a straight contour. Advantageously the first leg and the second leg form straight sides of a mesh. Especially advantageously the entire first leg and/or the entire second leg is embodied straight. In particular, the first leg and/or the second leg has a length of at least 1 cm, advantageously at least 2 cm, especially advantageously at least 3 cm, preferably no less than 5 cm and particularly preferably at least 7 cm. The first leg and the second leg may however also have any other lengths, in particular considerably greater lengths. The first leg and/or the second leg may, for example, have a length of no less than 10 cm or at least 15 cm or no less than 20 cm or at least 25 cm or an even greater length, in particular if the helix is embodied of a wire strand, a wire rope, a wire bundle or the like.

In another implementation of the invention it is proposed that the first leg extends at least section-wise in a first plane and the second leg extends at least section-wise in a second plane that is parallel to the first plane. In particular, at least two neighboring legs of the helix extend in parallel planes. Advantageously, in the transverse view the first leg extends in parallel to the second leg. The first leg and the further first leg preferably extend in the first plane and/or the second leg and/or the further second leg extend in the second plane. Preferably said first plane defines a front side of the wire netting and/or the second plane defines a rear side of the wire netting, or vice versa. This allows rendering a wire netting with a double-faced and/or double-walled structure available. Preferably in this way forces acting transversely to the netting may be absorbed effectively, involving a minimum deformation of the netting.

The further helix in particular comprises at least one further bending region, in a proximity of which the helix and the further helix intersect. Preferably the first bending region is connected, in particular hooked, with the further bending region. In particular, the further bending region connects the further first leg and the further second leg. The first leg preferably extends at least substantially parallel or parallel to the further first leg. Particularly preferably the second leg extends at least substantially parallel or parallel to the further second leg.

In an advantageous implementation of the invention it is proposed that the first helix and the second helix intersect perpendicularly in a proximity of the further bending region. In particular, the second gradient angle is 45° and an analogously defined further second gradient angle of the further bending region is also 45°. Preferably bending regions of the wire netting which are hooked with one another respectively intersect perpendicularly. In this way a high tensile strength of a connection between bending regions is achievable, in particular due to a direct force introduction and/or force transmission in intersection points. Furthermore, this allows maximizing a contact surface between hooked bending regions.

It is moreover proposed that the second gradient angle is smaller than the first gradient angle, in particular in case the first gradient angle is larger than 45°. Alternatively it is proposed that the second gradient angle is larger than the first gradient angle, in particular in case the first gradient angle is smaller than 45°. Preferably the second gradient angle is independent from the first gradient angle and is in particular advantageously exactly 45°, as has been mentioned above. In case of differently embodied bending regions being hooked with one another, the second gradient angles of the respective bending regions are advantageously chosen in such a way that the bending regions intersect perpendicularly. This allows rendering available connecting points featuring a high load-bearing capacity, independently from a mesh geometry.

It is further proposed that the first gradient angle is larger than 45°, advantageously larger than 50°, especially advantageously larger than 55° and preferably larger than 60°, resulting in particular in narrow meshes being implemented. In particular, the first interior angle of the mesh is in particular considerably greater than the second interior angle of the mesh. In this way a high tensile strength of a netting is achievable, in particular perpendicularly to a longitudinal direction of netting helices.

It is however also conceivable that the first gradient angle is smaller than 45°, advantageously smaller than 40°, especially advantageously smaller than 35° and preferably smaller than 30°, resulting in particular in wide meshes being implemented. In particular, the first interior angle of the mesh is in particular considerably smaller than the second interior angle of the mesh. In this way a high tensile strength of a netting is achievable, in particular in parallel to a longitudinal direction of netting helices. Moreover it is in this way possible to render a wire netting available for a slope protection of the like, which may be rolled out transversely to a slope, thus advantageously allowing quick installation for narrow areas that are to be secured.

In a preferred embodiment of the invention it is proposed that, in the longitudinal view, the bending region comprises at least one second transition zone which is connected to the second leg and has a second transition curvature differing from the bending curvature. Advantageously the first transition zone, the second transition zone and the bending zone together form the bending region. In particular, the bending region is implemented of the first transition zone, the second transition zone and the bending zone. Preferably the second transition zone is connected to the bending region in a one-part implementation. Especially preferentially the second leg is connected to the second transition zone, in particular in a one-part implementation. Preferably the helix is not curved, except for knots and bending regions. This allows rendering a helix geometry available which is variable and is adaptable to a requirement regarding a variety of parameters.

In a particularly preferred implementation of the invention it is proposed that the first transition curvature and the second transition curvature are identical. Advantageously the first transition zone and the second transition zone respectively comprise an identical portion of the bending region. This preferably allows rendering a wire netting available, the front side and rear side of which may be used in an exchangeable fashion.

It is furthermore proposed that, in the longitudinal view, the first transition zone and the second transition zone are embodied mirror-symmetrically, advantageously with respect to a symmetry plane in which the angle bisector of the second interior angle of the mesh extends, and/or which is arranged in parallel to the longitudinal direction of the helix. Preferably said symmetry plane is a main extension plane of the wire netting and/or of the helix. Preferentially the bending region is mirror-symmetrical in the longitudinal view, in particular with respect to said symmetry axis. This allows achieving advantageous mechanical properties of a bending region.

Beyond this it is proposed that the bending curvature is larger than the first transition curvature and/or than the second transition curvature. It is conceivable that the first transition curvature and/or the second transition curvature is at least substantially constant. Preferably, in the first transition zone and/or in the second transition zone the bending region merges into the first leg and/or into the second leg. Advantageously the first leg, the bending region and the second leg form a V-shaped section of the helix, wherein the bending region in particular forms a rounded tip of the section. This advantageously allows avoiding, in particular to a large extent, or at least reducing stress in the material caused by sudden geometry changes.

A high degree of hardness in a frontal direction and/or a high load-bearing capacity of connecting points of a netting is achievable if the bending zone, in particular the entire bending zone, follows a circular-arc-shaped course, in particular in the longitudinal view. Advantageously a curvature radius of the bending zone is at least substantially equivalent to a sum of a radius of the longitudinal element, respectively the wire, and a radius of the bending mandrel.

In particular, for the reverse bend test C is a factor of precisely 400 $N^{0.5}$ $mm^{0.5}$. It is also conceivable that a greater C is chosen, in particular to achieve a higher load-bearing capacity of a helix. For example, C may be a factor of at least 500 $N^{0.5}$ $mm^{0.5}$ or no less than 750 $N^{0.5}$ $mm^{0.5}$ or at least 1000 $N^{0.5}$ $mm^{0.5}$ or no less than 1500 $N^{0.5}$ $mm^{0.5}$ or even greater. In particular, the factor may be chosen specific for an application, wherein a greater factor will result in selecting a wire breaking less easily in case of bending, and thus in particular to a wire netting with a higher level of non-destructive deformability.

Furthermore, according to the invention a method for producing a wire netting according to the invention, in particular a safety net, with a plurality of helices which are braided with one another, is proposed, wherein a wire suitable for manufacturing, which is in particular made of a high-tensile steel, is identified at least via the method according to the invention for identifying a suitable wire, and wherein at least one helix is manufactured of at least one single wire, a wire bundle, a wire strand, a wire rope and/or another longitudinal element with the identified wire by bending. This advantageously allows largely avoiding time-consuming test runs. Moreover in this way a high-grade wire netting is producible.

It is further proposed that the first partial characteristic curve runs over a press-path value range that is equivalent to at least a quarter, advantageously at least a third, especially advantageously at least half of the transverse extension of the helix. In particular, a transverse extension of the test piece of the helix is equivalent to a transverse extension of the helix. This advantageously allows rendering a wire netting available which is capable of receiving forces acting in an impact partly elastically and/or non-destructively over a wide range.

In an advantageous implementation of the invention it is proposed that an approximately linearly-extending second partial characteristic curve with a second gradient that is greater than the first gradient follows, in particular directly follows, the first partial characteristic curve. In particular, the second gradient is at least 1.2 times, advantageously no less than 1.5 times, especially advantageously at least twice and preferably no less than three times as great as the first gradient. In particular, the second gradient is maximally ten times, advantageously no more than eight times, especially advantageously maximally six times and preferentially no more than five times as great as the first gradient In this way, force peaks occurring in case of a load may be advantageously absorbed by a wire netting.

An adaptive force intake and/or energy intake of a wire netting is achievable if the second gradient is no more than four times as great as the first gradient. In particular, in this way damages by abruptly decelerated, impacted objects are avoidable as a deceleration is effected in at least two steps.

Beyond this it is proposed that the spring characteristic curve has a kink in a transition region between the first partial characteristic curve and the second partial characteristic curve, which in particular allows achieving a spontaneous response in case of an impact. A "kink" is in particular to mean, in this context, a spontaneous, in particular a jump-like of jump-style change in a gradient. In particular, the transition region extends over a press path value range that corresponds to maximally 5%, advantageously no more than 3%, especially advantageously no more than 2% and preferably maximally 1% of the transverse extension of the helix.

It is also proposed that the second partial characteristic curve extends over a press path value range that corresponds to at least a fifth, advantageously no less than a quarter, especially advantageously at least a third of the transverse extension of the helix. Preferably the second partial characteristic curve extends over a press path value range that is smaller than a corresponding press path value range of the first partial characteristic curve. In this way, in a second force accommodation zone of a wire netting, great forces may be absorbed in a controlled manner involving a comparably smaller deformation than in a first force accommodation zone of the wire netting.

In a preferred implementation of the invention it is proposed that the second partial characteristic curve is directly followed by a convexly curved third partial characteristic curve. In particular, the third partial characteristic curve has a gradient increasing, in particular continuously, in particular mathematically continuously, with an increase of the press path. It is conceivable that the third partial characteristic curve follows a polynomial, in particular a parabolic or an exponential course. In particular, the third partial characteristic curve extends over a press path value range corresponding to at least a tenth, advantageously at least an eighth, especially advantageously at least a sixth and preferably at least a quarter of the transverse extension of the helix. Preferably the third partial characteristic curve extends over a press path value range that is smaller than a corresponding press path value range of the second partial characteristic curve. In this way extreme forces may be accommodated safely, in particular by way of a controlled deformation of a wire netting, respectively of the helices thereof.

It is further proposed that a transition between the second partial characteristic curve and the third partial characteristic curve is kink-free. In particular, the gradient of the second partial characteristic curve continuously merges into the gradient of the third partial characteristic curve. Preferably the spring characteristic curve is composed of the first partial characteristic curve, the second partial characteristic curve, which in particular directly follows the first partial characteristic curve, and the third partial characteristic curve, which in particular directly follows the second partial characteristic curve. This advantageously allows avoiding a suddenly occurring damaging of a wire netting, e.g. in case of an impact.

Principally it is conceivable that the first partial characteristic is directly followed by a partial characteristic curve which, in terms of its course, approximately or precisely corresponds to the third partial characteristic curve. It is in particular conceivable that the spring characteristic curve is free of a second linear partial characteristic curve.

Moreover it is proposed that the geometry adjusting unit comprises a transverse stroke unit, which is configured to change a relative position of the bending table with respect to the feed axis, along a main extension direction in a transverse stroke direction of the bending mandrel, periodically and/or in a manner synchronized with a circulation of the bending table about the bending mandrel, in particular during manufacturing of the helix. In particular, the transverse stroke unit comprises at least one conveying element, which conveys the helix blank to the bending table. In particular, the conveying element is supported displaceably, with respect to the bending table, in the transverse stroke direction. Advantageously the transverse stroke unit comprises at least one coupling element, which couples a movement of the conveying element, in particular mechanically, to the circulation of the bending table about the bending mandrel. Preferentially the bending table is, at a start of the bending and/or following the forward-feeding of the helix blank, in a start position of the bending table. Especially preferentially the conveying element is, at a start of the bending and/or following the forward displacement of the helix blank, in a start position of the conveying element. In particular, during a circulation of the bending table about the bending mandrel, the bending table and the conveying element are at least once in their respective start positions simultaneously. Advantageously, during a circulation of the bending table about the bending mandrel, the conveying element is deflected out of its start position, in parallel to the transverse stroke direction, away from the bending table. Especially advantageously, in said circulation of the bending table the conveying element is then moved back into its start position. In particular, the transverse stroke unit is configured to provide a bending region generated in bending with the second gradient angle. In particular, the transverse stroke unit is configured to generate an adjustable transverse stroke. This advantageously allows a precise adjustment of a geometry of a bending region by adapting a transverse stroke.

In an advantageous implementation of the invention it is proposed that the geometry adjusting unit comprises an abutment unit with at least one abutment element defining a maximum feed-forward position for the helix blank. In particular, the abutment unit is configured to adjust a length of the first leg and/or a length of the second leg. Advantageously, in the forward feeding, the feed unit feeds the helix blank, in particular a respective most recently bent bending region, forward up to the abutment element. In particular, in a forward-fed state, the helix blank, in particular the respective most recently bent bending region, abuts on the abutment element. Preferentially, prior to bending, the helix blank is fed forward up to the maximum feed-forward position. In this way advantageously a helix geometry, in particular a leg length, may be adjusted precisely and/or easily and/or reliably.

In an especially advantageous implementation of the invention it is proposed that the abutment element is supported in a manner completely circulating about the bending mandrel, in particular circulating on a circular path. Preferably a movement of the bending table and a movement of the abutment element about the bending mandrel are synchronized, in particular during manufacturing of the helix. This allows facilitating a precise forward-feeding at a high manufacturing speed.

It is moreover proposed that, in a circulation of the bending table, a position of the bending table with respect to the abutment element is variable. Advantageously the abutment element runs in advance of the bending table during the forward-feeding and/or prior to the bending. In particular, during a circulation of the bending table about the bending mandrel, the helix blank is already situated in the maximum feed-forward position before the bending table is in its start position. Advantageously the abutment element abuts on the bending table during bending. Especially advantageously a position of the abutment element with respect to the bending table is constant during bending. In this way a movement flow allowing high-level precision and/or a high speed of manufacturing.

A precise positioning of a blank prior to bending is achievable if the abutment element comprises an abutment surface that is curved concavely, in particular curved in the shape of a circular arc. In particular, the abutment surface is curved concavely, in particular curved in the shape of a circular arc, in two directions, which advantageously extend perpendicularly to one another. Preferably, in a circulation of the abutment element about the bending mandrel, a distance between the abutment surface and the bending mandrel is constant. Preferentially the abutment surface is implemented as a surface of a groove. The groove is advantageously curved about the bending mandrel in a circulation direction. Particularly advantageously the abutment surface is curved concavely in a direction that is perpendicular to a longitudinal direction of the groove. In particular, a curvature of the abutment surface in a longitudinal view approximately corresponds to a curvature of the bending region. In particular, the groove is configured for centering the helix blank and/or the most recently bent bending region, in particular toward an end of the forward-feeding and/or in the maximum feed-forward position of the helix blank.

It is further proposed that in at least one forward-feed operating state, in which a forward-feeding of the helix blank is effected, a position of the abutment element with respect to the feed axis, and in particular with respect to the bending mandrel, is variable. In particular, in the forward-feed operating state, the abutment element circulates about the bending mandrel with a constant angular velocity. In this way a precise abutment for a blank may be made available by means of a moved structural component, in particular by a rotating structural component.

In a preferred implementation of the invention it is proposed that the bending table is supported pivotally about a pivot axis which itself circulates about the bending mandrel during circulation of the bending table about the bending mandrel. Advantageously the pivot axis is arranged parallel to the longitudinal axis of the bending mandrel. Especially advantageously the bending table is pivoted about the pivot axis after bending. In particular, in pivoting about the pivot axis, the bending table carries out an evasive movement, as a result of which the bending table is conveyable underneath the helix blank when circulating about the bending mandrel. In particular, during part of its circulation about the bending mandrel the bending table is in a pivoted position. This allows advantageously providing a continuously circulating bending table facilitating quick and precise manufacturing.

In a particularly preferred embodiment of the invention it is proposed that for the purpose of bending a helix blank the bending unit is configured with at least one wire which is made of a high-tensile steel.

Helixes which are straight in themselves and/or not twisted in themselves are advantageously manufacturable if the bending unit is configured to bend the helix blank by more than 180° in a circulation of the bending table. In particular, the bending unit is configured to overbend and/or overpress the helix blank in bending, which may be necessary in particular in case of longitudinal elements with a high-tensile wire, in particular because of a partially elastic behavior and/or resilience of such longitudinal elements. Advantageously the bending unit is configured to generate bending regions which are bent by 180°. Advantageously, following the bending, the bending table is pivoted by an angle greater than 180°. Especially advantageously the bending unit is configured to adjust an overbend angle. In particular, during bending the bending table presses against the helix blank, advantageously while, in its circulation, the bending table sweeps over an angle range that is greater than 180° by an overbend angle. In particular, an overbend angle may be, for example, up to 1° or up to 2° or up to 5° or up to 10° or up to 15° or up to 20° or up to 30° or more, in particular depending on spring characteristic curves of the helix blank. It is also conceivable that the overbend angle is adjustable via an adjustment of the bending unit.

An inadvertent subsequent bending is avoidable and/or a high precision of manufacturing is achievable if the geometry adjusting unit comprises a holding unit with at least one holding element, which at least partly fixates the helix, viewed from the bending mandrel, behind the bending table in bending and in particular in overbending as well. In particular, the holding element restricts a movability and/or bendability of the helix in at least one direction, in particular toward a half-space. Advantageously the holding element holds the helix in a proximity of a leg abutting on the most recently bent bending region. In particular, the holding element partly engages around the helix, in particular in a direction toward a main extension plane of the bending table. The holding element is advantageously embodied fork-like. In particular, in a bending of the helix blank about the bending mandrel, the bending table pivots the entire already bent helix about an axis that is parallel to the longitudinal axis of the helix, wherein the holding element advantageously stabilizes the helix in said pivoting.

A continuous support of a helix while it is bent may be obtained if the holding element is supported in such a way that it fully circulates about the bending mandrel. In particular, the holding element circulates about the bending mandrel in a manner synchronized with the circulation of the bending table, in particular during manufacturing of the helix.

In a further implementation of the invention it is proposed that the holding element is supported pivotally about a pivot axis, the pivot axis itself circulating about the bending mandrel during a circulation of the holding element about the bending mandrel. In particular, the holding element abuts on the helix only during part of a circulation of the holding element about the bending mandrel. Advantageously the holding element pivots about its pivot axis during its circulation about the bending mandrel, while moving away from the helix. Especially advantageously the holding element is during the forward-feeding arranged touch-free with respect to the helix and to the helix blank. This in particular allows achieving a high manufacturing speed. Moreover, in this way a deceleration of moved components during manufacturing may be largely dispensed with in a time-efficient and/or energy-effective fashion.

In a preferred embodiment of the invention it is proposed that the holding element is supported on the bending table. In particular, the pivot axis of the bending table and the pivot axis of the holding element extend in parallel, and preferentially in parallel to the longitudinal axis of the bending mandrel. In particular, the pivot axis of the holding element extends in the bending table and/or in a suspension of the bending table. Preferably the geometry adjusting unit comprises at least one slotted link for the bending table. Especially preferentially the geometry adjusting unit comprises at least one further slotted link for the holding element. Advantageously, during manufacturing of the helix the bending table and the holding element circulate about the bending mandrel synchronously and are pivoted with respect to the helix blank at different points in time.

The invention furthermore comprises a method for manufacturing a wire netting according to the invention, in particular a safety net, comprising a plurality of helices which are braided with one another and at least one of which is manufactured of at least one helix blank, namely a single wire, a wire bundle, a wire strand, a wire rope and/or another longitudinal element with at least one wire, by means of at least one bending device according to the invention. In this way in particular a high speed of manufacturing and a high manufacturing precision may be achievable.

A wire netting according to the invention, a bending device according to the invention and a method according to the invention are herein not to be restricted to the applications and implementation forms described above. In particular, to fulfill a functionality herein described, a wire netting according to the invention, a bending device according to the invention and a method according to the invention may comprise a number of respective elements and/or structural components and/or units and/or method steps that differs from a number herein mentioned.

DRAWINGS

Further advantages will become apparent from the following description of the drawings. In the drawings various exemplary embodiments of the invention are depicted. The drawings, the description and the claims contain a plurality of features in combination. Someone skilled in the art will purposefully also consider the features separately and will find further expedient combinations.

Figure 2:
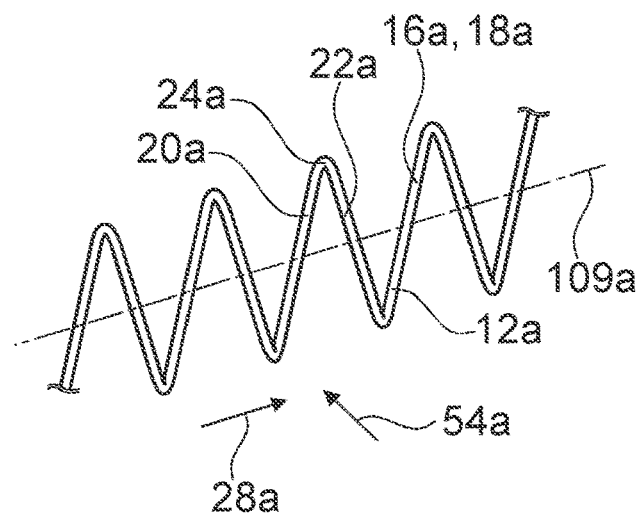
Figure 3:
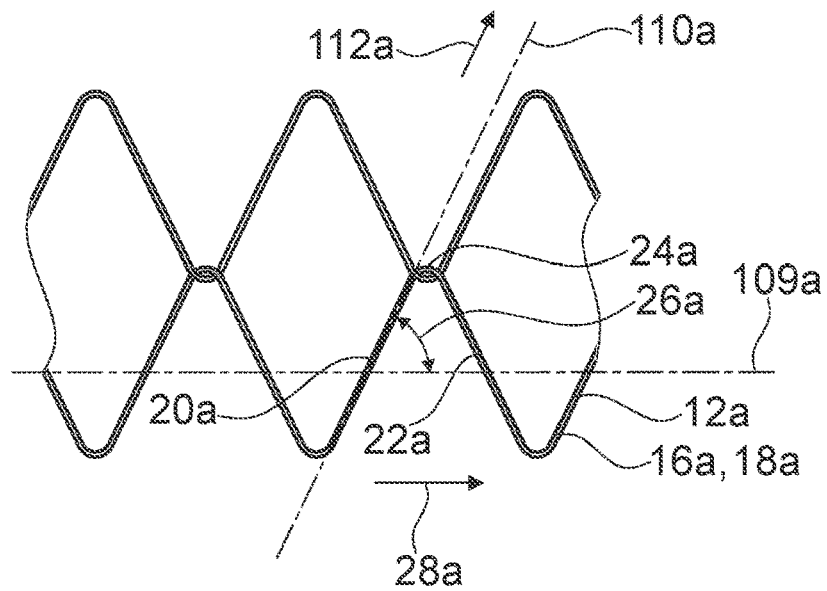
Figure 6:
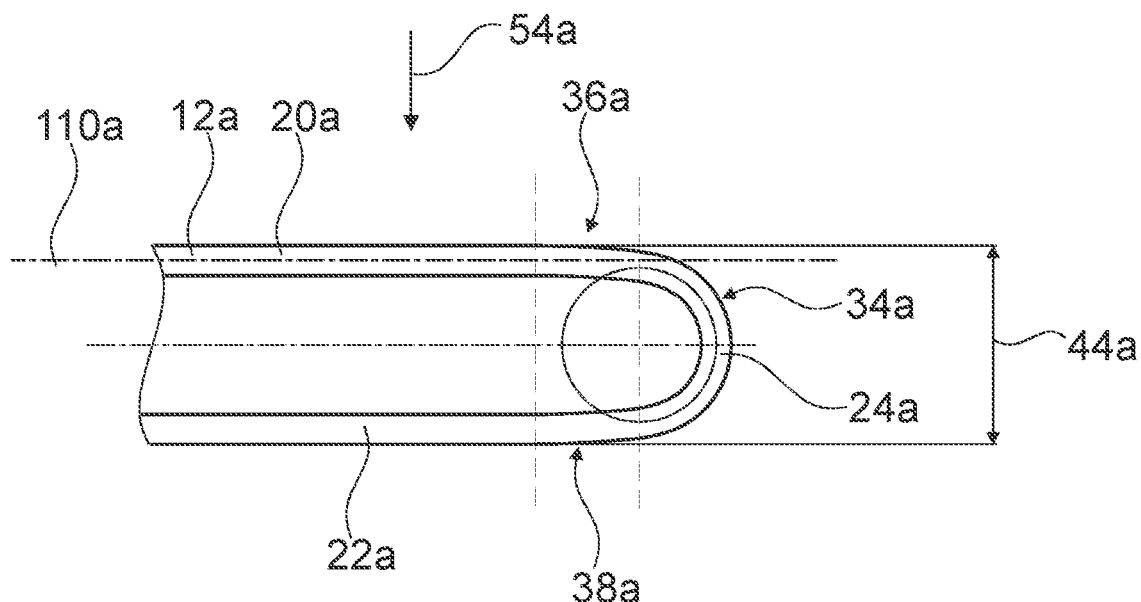
Figure 7:
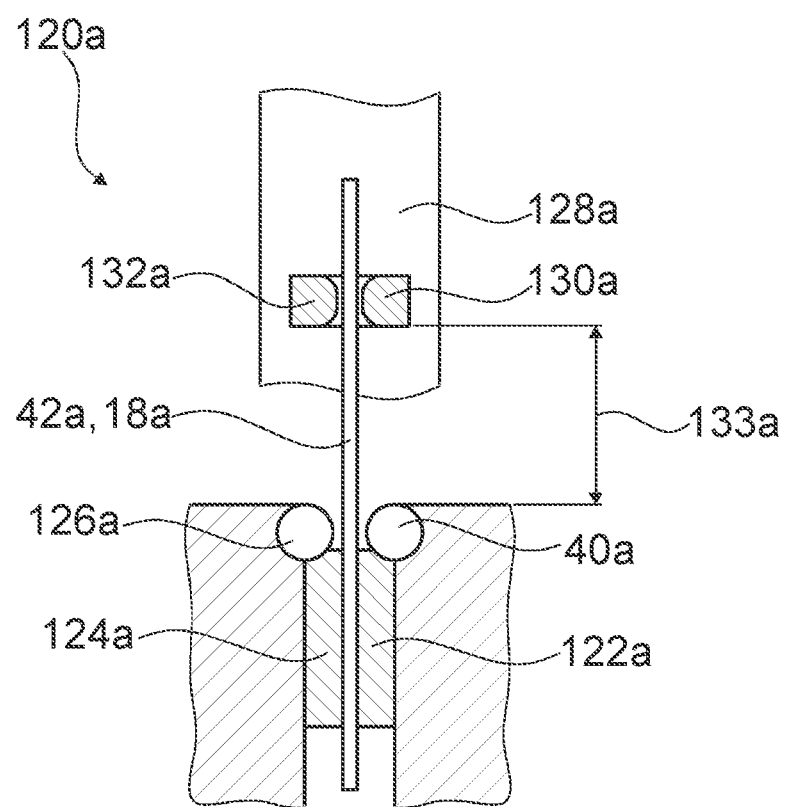
Figure 8:
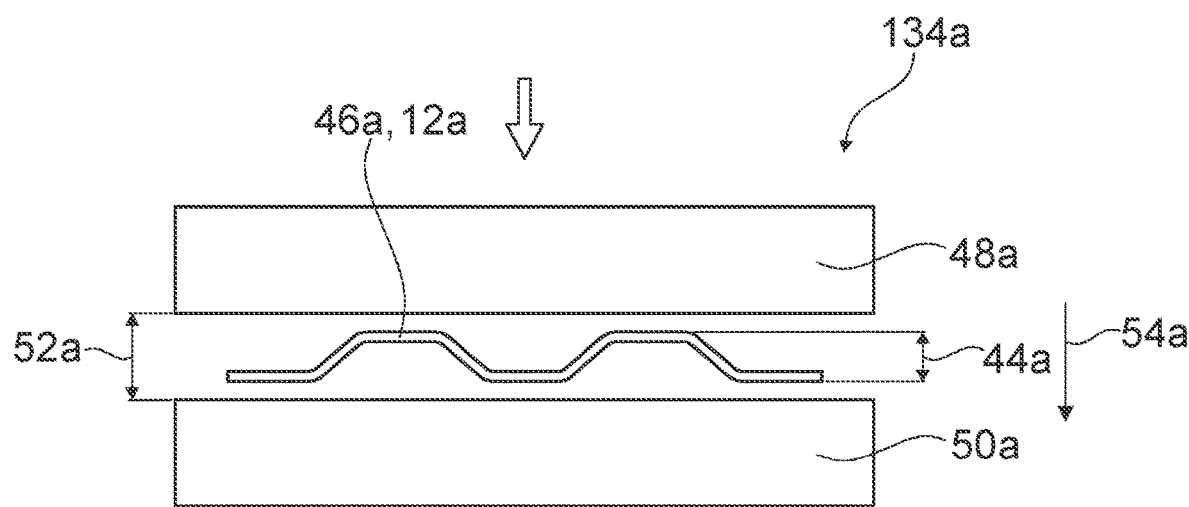
Figure 9:
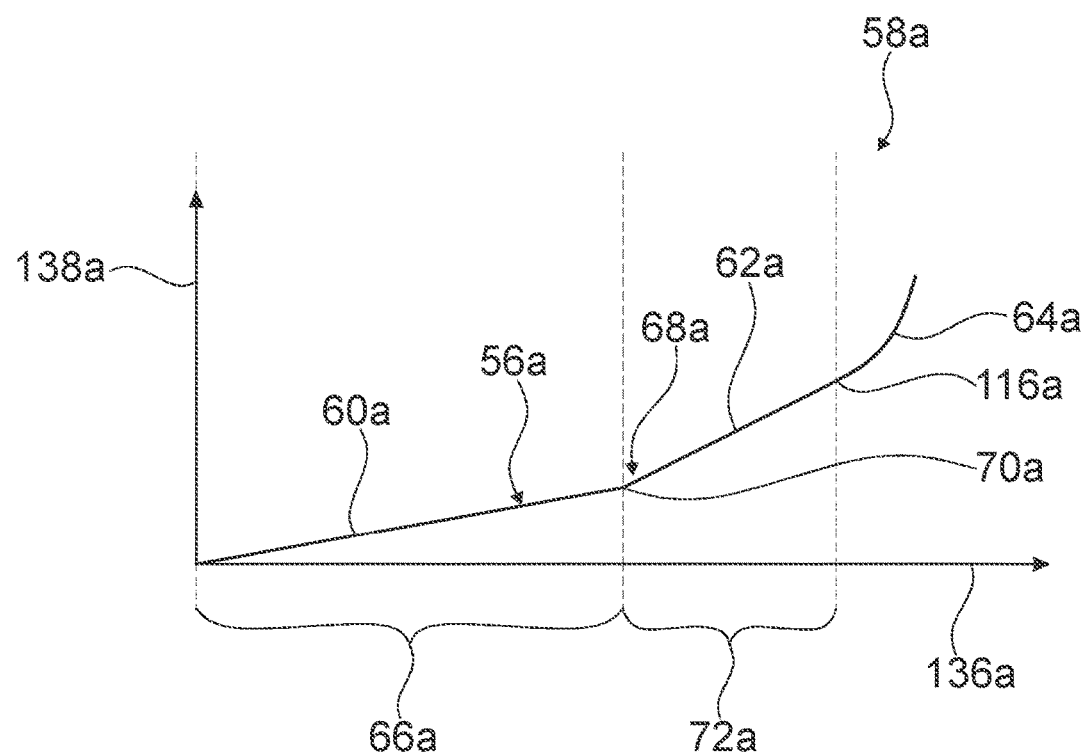
Figure 10:
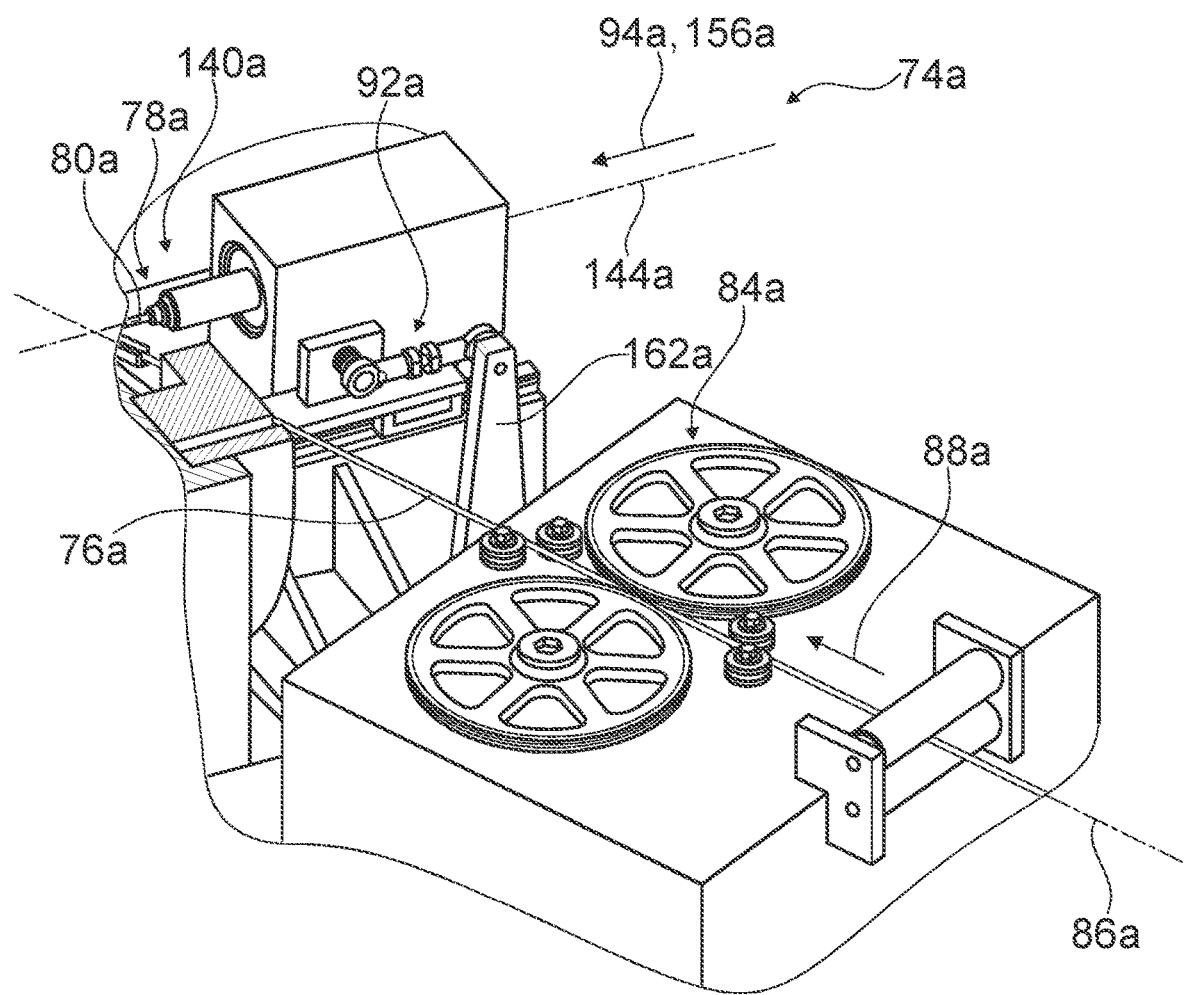
Figure 11:
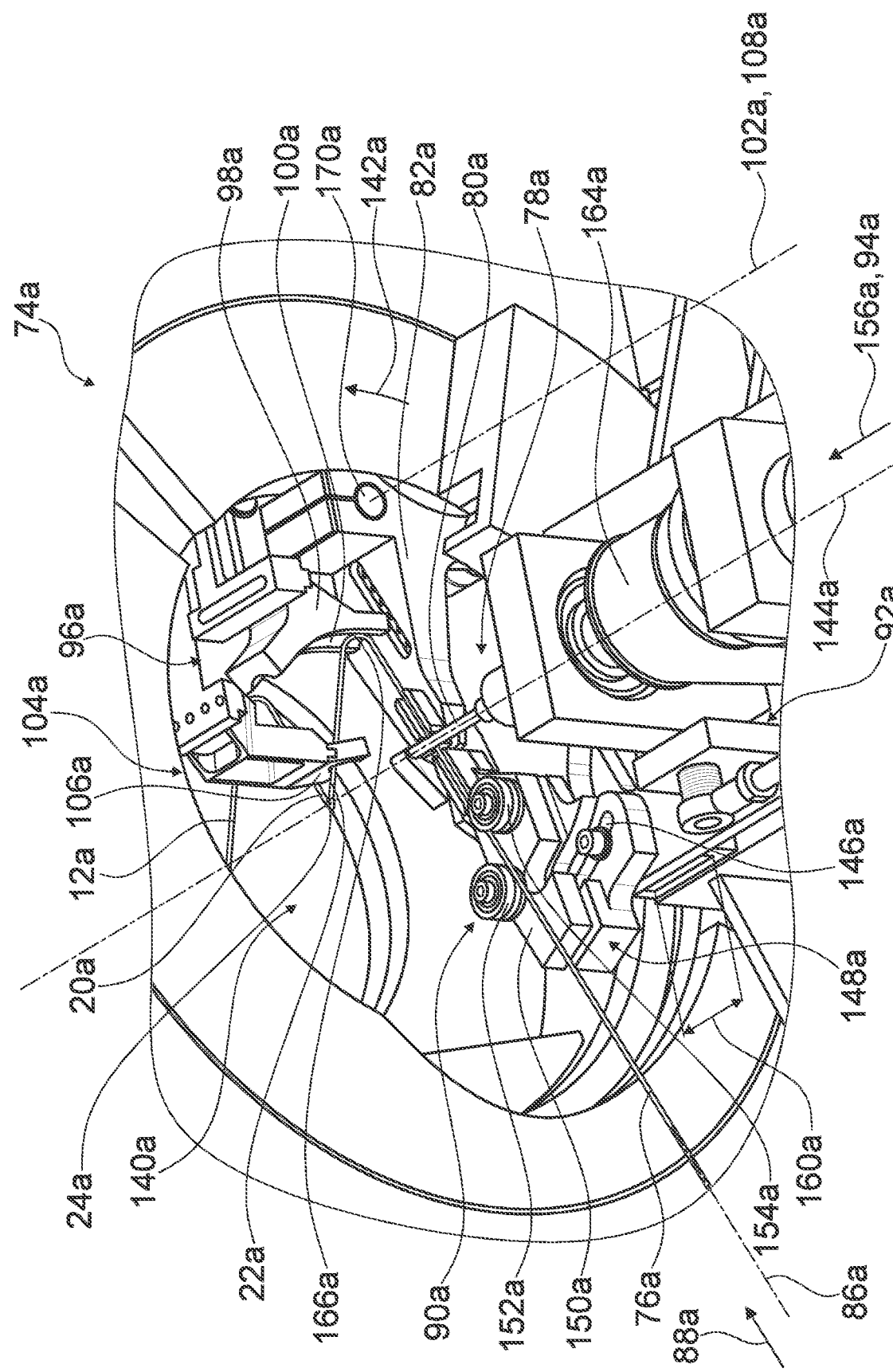
Figure 12:
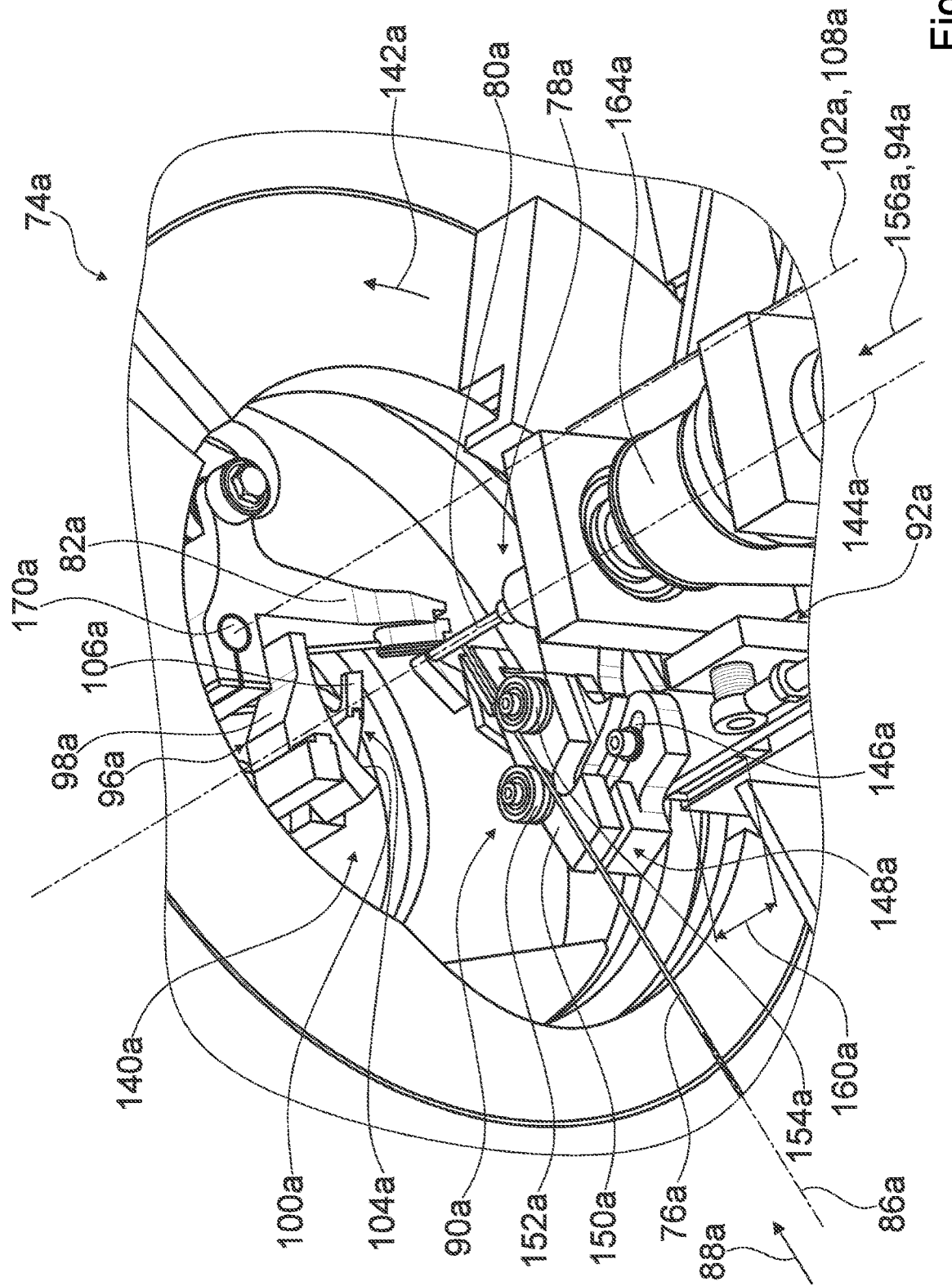
Figure 13:
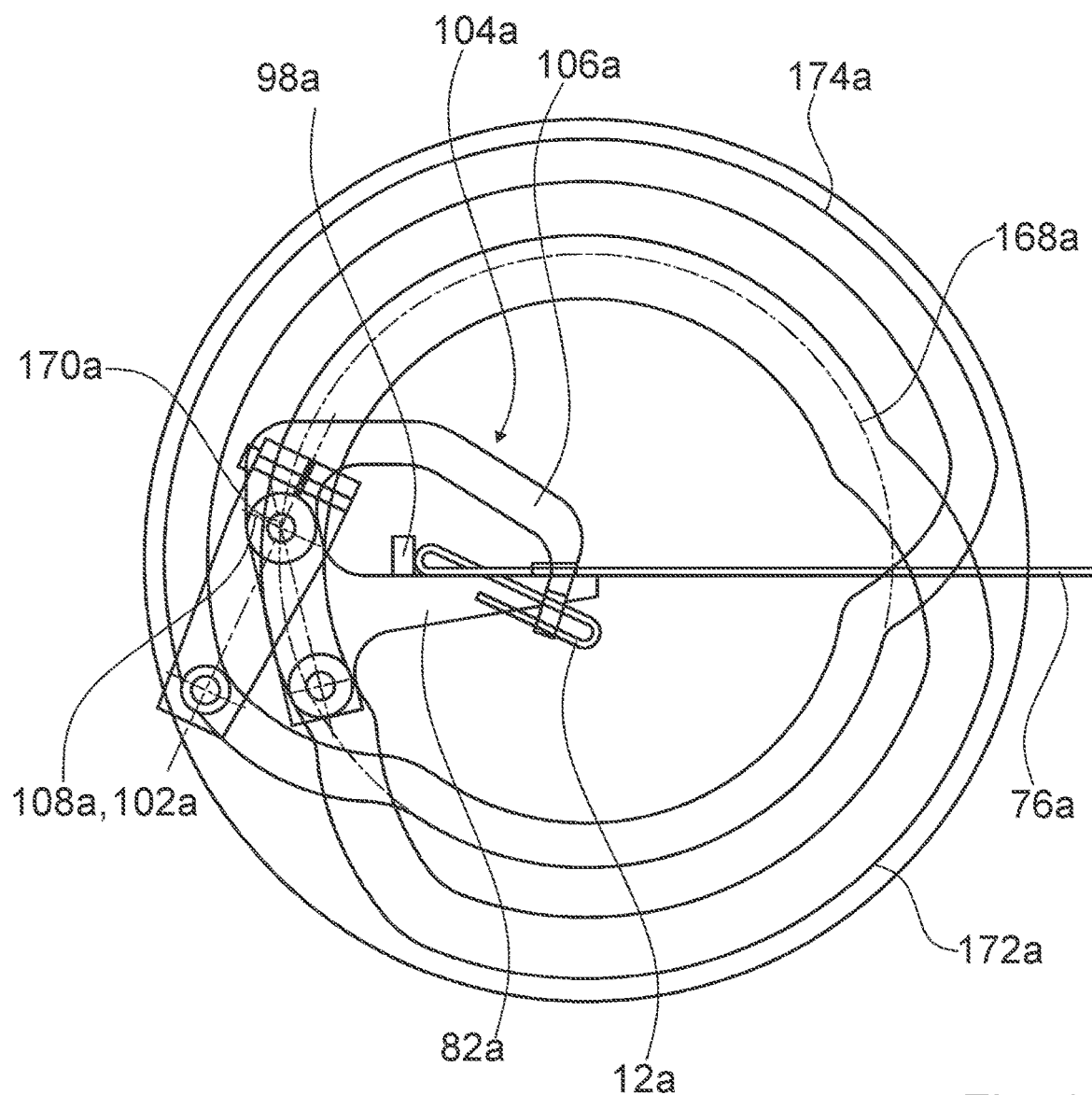
Figure 14:
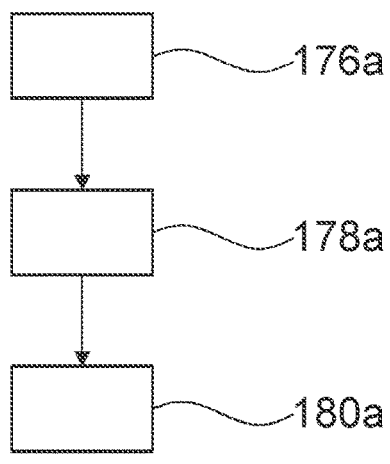
Figure 15:
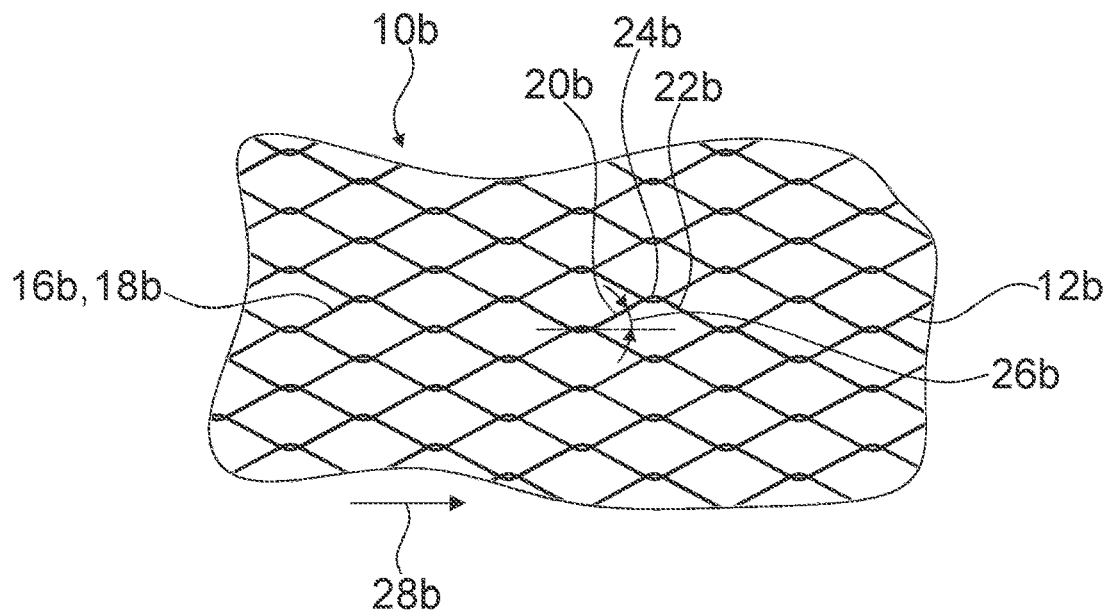
Figure 16:
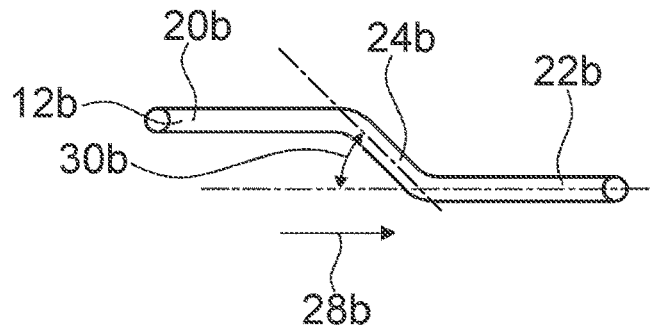
Figure 17:
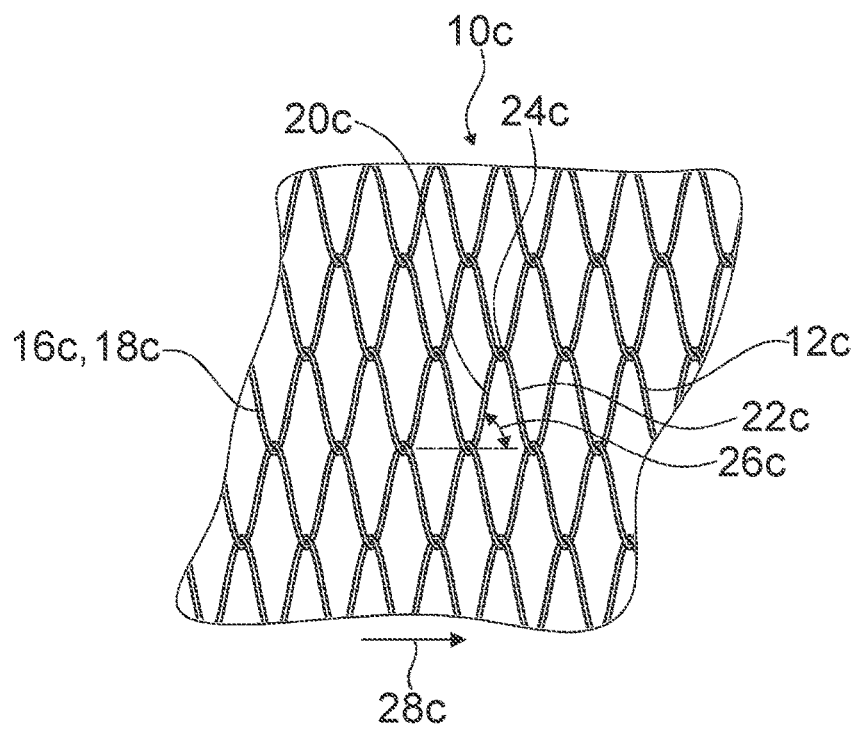
Figure 18:
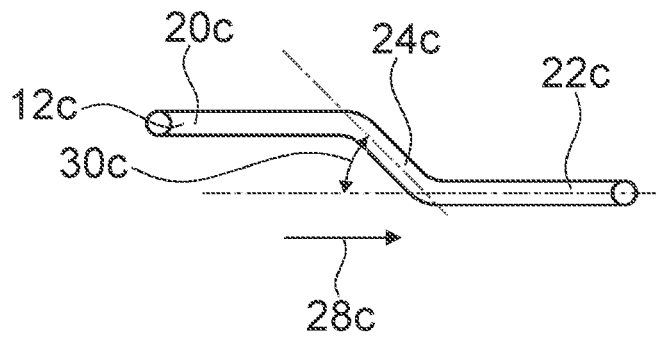
Figure 19:
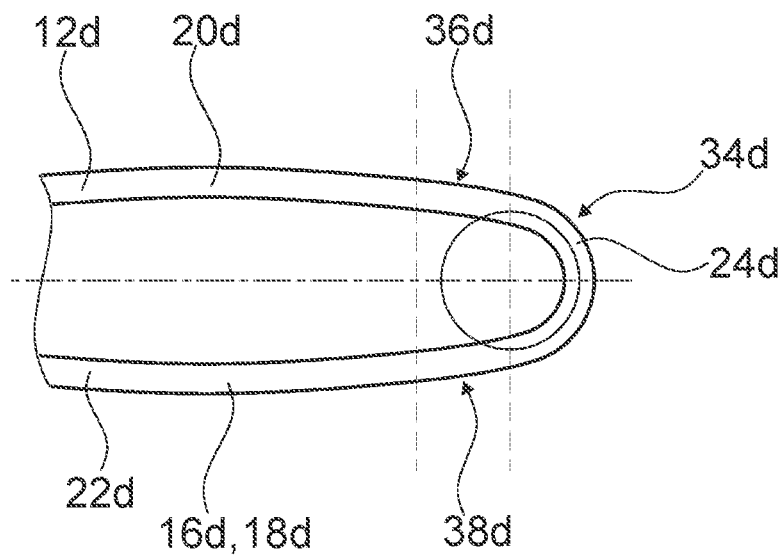
Figure 20:
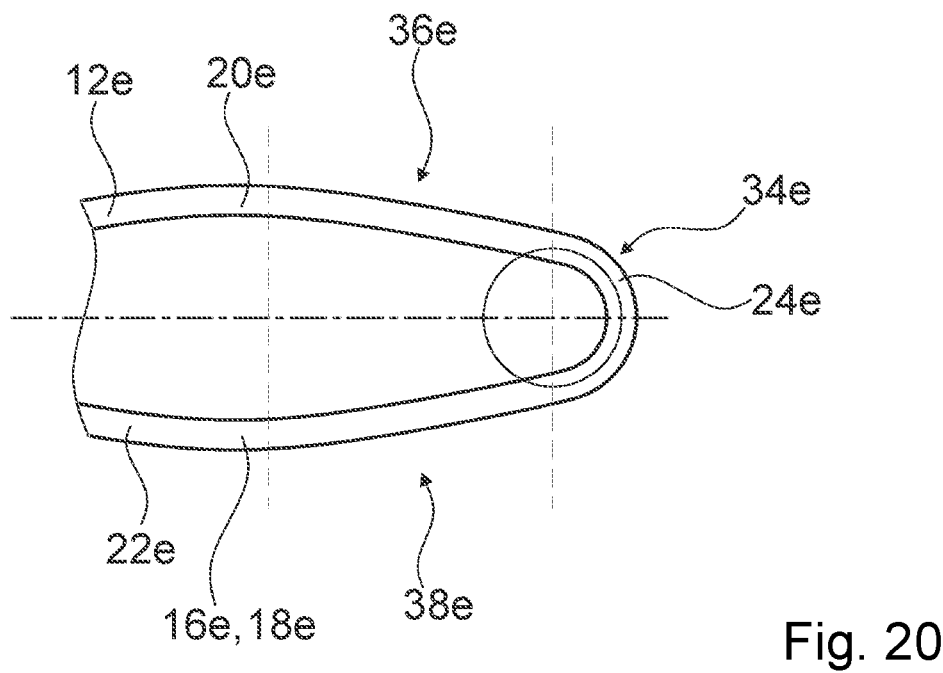
Figure 21:
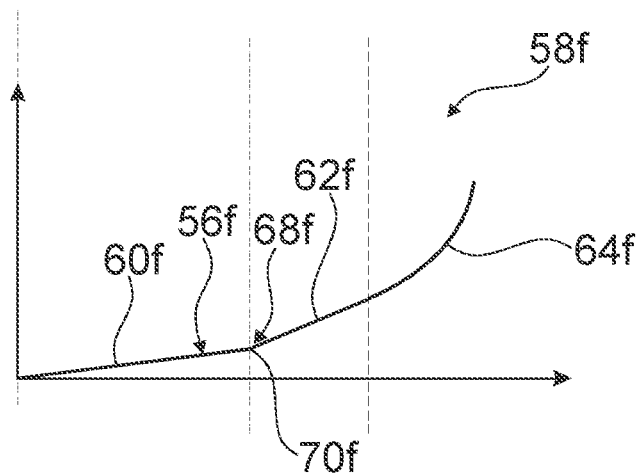
Figure 22:
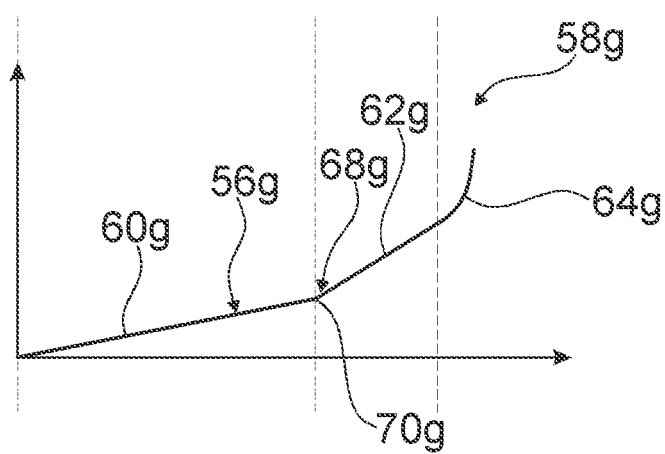
Figure 23:
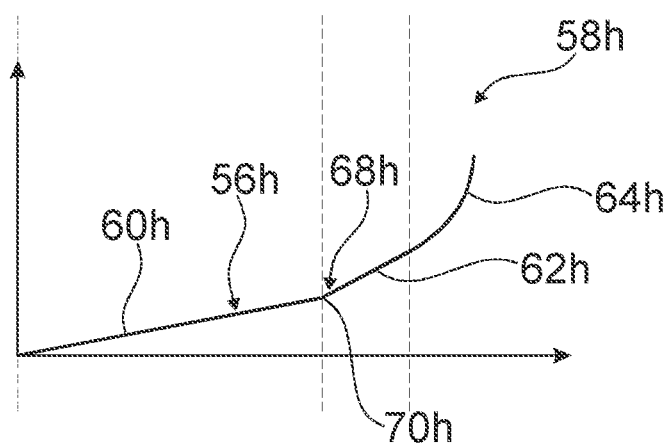
Figure 24:
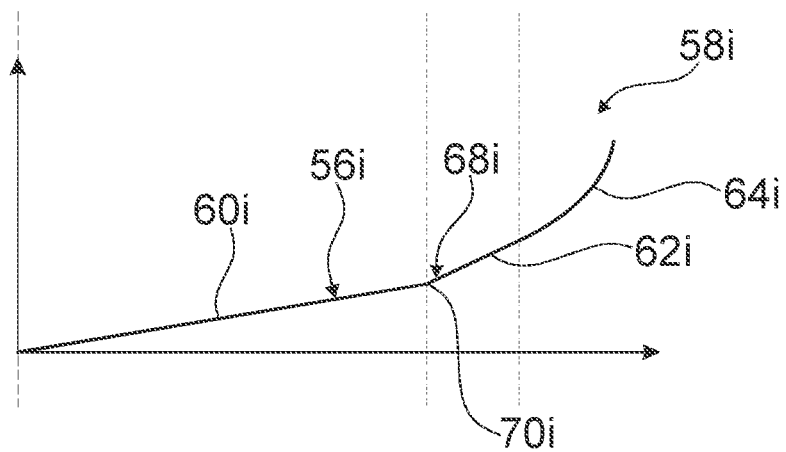
Figure 25:
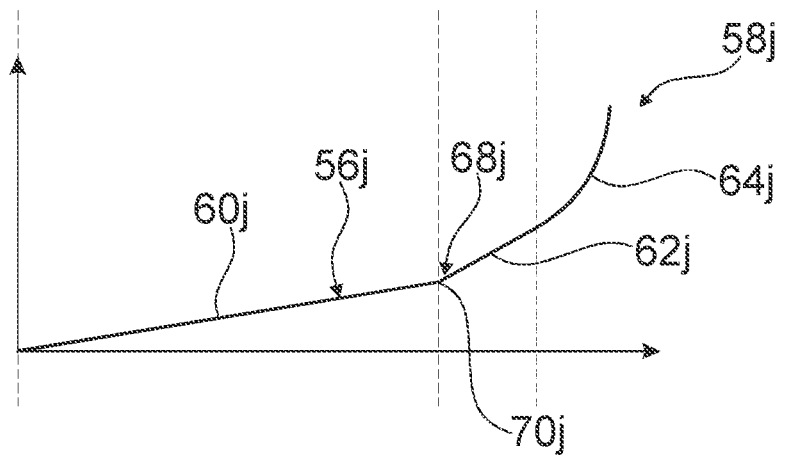

It is shown in:

FIG. 1 a portion of a wire netting in a schematic front view,

FIG. 2 a portion of a helix of the wire netting in a perspective view,

FIG. 3 another portion of the wire netting in a schematic front view,

FIG. 4 two legs and a bending region of the helix in different views,

FIG. 5 two interconnected bending regions of two helices in different views,

FIG. 6 the helix, viewed in a longitudinal direction of the helix, in a schematic representation, FIG. 7 a bend test device for carrying out a reverse bend test, in a schematic representation, FIG. 8 a pressing device for carrying out a press test, in a schematic representation, FIG. 9 a spring characteristic curve of a test piece of the helix, in a schematic diagram, FIG. 10 a bending device for manufacturing a wire netting, in a perspective view, FIG. 11 a bending space of the bending device in a first operating state, in a perspective view, FIG. 12 the bending space in a second operating state, in a perspective view, FIG. 13 slotted links of a bending table and of a holding element of the bending device, in a schematic side view, FIG. 14 a schematic flow chart of a method for manufacturing the wire netting, FIG. 15 a second wire netting in a schematic front view, FIG. 16 a bending region of a helix of the second wire netting, in a schematic representation, FIG. 17 a third wire netting in a schematic front view, FIG. 18 a bending region of a helix of the third wire netting, in a schematic representation, FIG. 19 a helix of a fourth wire netting, viewed in a longitudinal direction of the helix, in a schematic view, FIG. 20 a helix of a fifth wire netting, viewed in a longitudinal direction of the helix, in a schematic view, FIG. 21 a spring characteristic curve of a test piece of a helix of a sixth wire netting, in a schematic diagram, FIG. 22 a spring characteristic curve of a test piece of a helix of a seventh wire netting, in a schematic diagram, FIG. 23 a spring characteristic curve of a test piece of a helix of an eighth wire netting, in a schematic diagram, FIG. 24 a spring characteristic curve of a test piece of a helix of a ninth wire netting, in a schematic diagram, and FIG. 25 a spring characteristic curve of a test piece of a helix of a tenth wire netting, in a schematic diagram.

DESCRIPTION OF THE EXEMPLARY EMBODIMENTS

FIG. 1 shows a portion of a wire netting 10a in a schematic front view. The wire netting 10a is implemented as a safety net. The wire netting 10a shown may be used, for example, as a slope protection, as a snow-slide protection net, as a catch fence or the like. The wire netting 10a comprises a plurality of helices 12a, 14a which are braided with one another, in particular a helix 12a and a further helix 14a. In the present case the wire netting 10a comprises a plurality of identically implemented helices 12a, 14a, which are twisted into each other and form the wire netting 10a.

FIG. 2 shows a portion of the helix 12a of the wire netting 10a in a perspective view. FIG. 3 shows another portion of the wire netting 10a in a schematic front representation. The helix 12a is manufactured of a longitudinal element 16a with at least one wire 18a. In the present case the longitudinal element 16a is embodied as a single wire. The wire 18a implements the longitudinal element 16a in the present case. The longitudinal element 16a is bent to form the helix 12a. The helix 12a is embodied in a one-part implementation. The helix 12a is manufactured of a single piece of wire. In the present case the wire 18a has a diameter d of 3 mm. It is also conceivable that a longitudinal element is implemented as a wire bundle, a wire strand, a wire rope or the like. Moreover it is conceivable that a wire has a different diameter, e.g. less than 1 mm or approximately 1 mm or approximately 2 mm or approximately 4 mm or approximately 5 mm or approximately 6 mm or has an even greater diameter.

The helix 12a comprises a first leg 20a, a second leg 22a and a bending region 24a connecting the first leg 20a and the second leg 22a. In the present case the helix 12a comprises a plurality of first legs 20a, a plurality of second legs 22a and a plurality of bending regions 24a, not all of which are given a reference numeral for the sake of better overview. Furthermore, in the present case the first legs 20a are implemented at least substantially identically to each other. In the present case the second legs 22a are also implemented at least substantially identically to each other. Moreover, in the present case the bending regions 24a are implemented at least substantially identically to each other. Therefore, in the following the first leg 20a, the second leg 22a and the bending region 24a are described in detail by way of example. It is of course conceivable that a wire netting comprises differing first legs and/or differing second legs and/or differing bending regions.

The helix 12a has a longitudinal direction 28a. The helix 12a has a longitudinal axis 109a extending in parallel to the longitudinal direction 28a. The longitudinal direction 28a is equivalent to a main extension direction of the helix 12a. In a front view perpendicularly to a main extension plane of the helix 12a, the first leg 20a extends featuring a first gradient angle 26a with respect to the longitudinal direction 28a of the helix 12a. In particular, the front view is a view in a frontal direction 54a. The first leg 20a has a longitudinal axis 110a. The longitudinal axis 110a of the first leg 20a extends in parallel to a main extension direction 112a of the first leg 20a. In FIG. 3 the helix 12a is shown in the front view. The longitudinal axis 109a of the helix 12a and the longitudinal axis 110a of the first leg 20a include the first gradient angle 26a. The first leg 20a has in the present case a length of approximately 65 mm. The second leg 22a has in the present case a length of approximately 65 mm.

FIG. 4 shows a portion of the helix 12a comprising the first leg 20a, the second leg 22a and the bending region 24a in a variety of views. FIG. 4a illustrates a view in the longitudinal direction 28a of the helix 12a. FIG. 4b shows the first leg 20a, the second leg 22a and the bending region 24a in a transverse view perpendicularly to the longitudinal direction 28a of the helix 12a and in the main extension plane of the helix 12*a*. FIG. 4*c* illustrates a view in the frontal direction 54*a*. FIG. 4*d* shows a perspective view. In the transverse view, the bending region 24*a* extends at least section-wise with a second gradient angle 30*a* with respect to the longitudinal direction 28*a* of the helix 12*a*, which is different from the first gradient angle 26*a*. In the transverse view the bending region 24*a* has a longitudinal axis 114*a*. The longitudinal axis 114*a* of the bending region 24*a* and the longitudinal axis 109*a* of the helix 12*a* include the second gradient angle 30*a*.

The wire 18*a* is at least partly made of a high-tensile steel. The wire 18*a* is embodied as a high-tensile steel wire. The wire 18*a* has a tensile strength R of at least 800 N mm$^{-2}$. In the present case the wire 18*a* has a tensile strength of approximately 1770 N mm$^{-2}$. Of course, as has been mentioned above, other tensile strengths are also conceivable, in particular even tensile strengths of more than 2200 N mm$^{-2}$. It is in particular conceivable that a wire is made of super high-tensile steel.

The second gradient angle 30*a* differs from the first gradient angle 26*a* by at least 5°. The second gradient angle 30*a* has a value between 25° and 65°. Furthermore the first gradient angle 26*a* is greater than 45°. In the present case the first gradient angle 26*a* is approximately 60°. Furthermore, in the present case the second gradient angle 30*a* is approximately 45°. The second gradient angle 30*a* is smaller than the first gradient angle 26*a*.

In the transverse view, the bending region 24*a* follows at least section-wise an at least approximately straight contour. In the present case a large part of the bending region 24*a* follows a straight contour in the transverse view.

In the transverse view, the helix 12*a* follows at least section-wise a stepped contour. The stepped contour is obliquely-stepped.

Figure 4A:
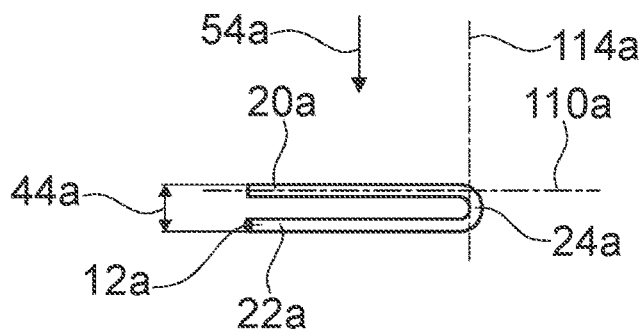
Figure 4B:
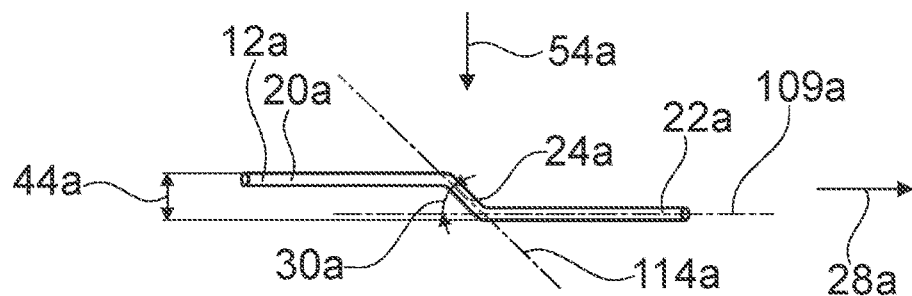
Figure 4C:
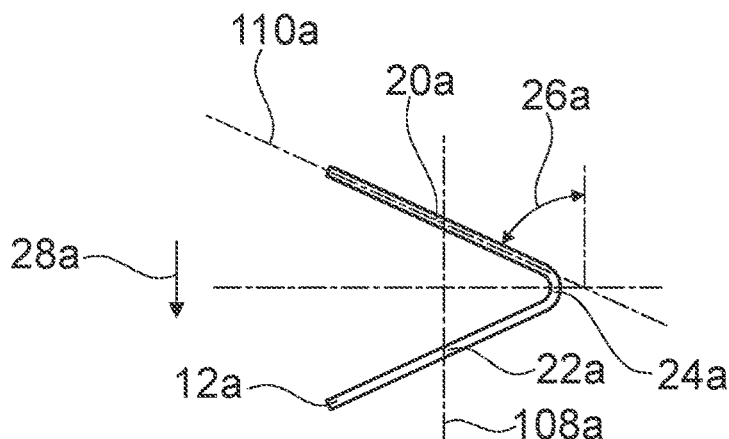
Figure 4D:
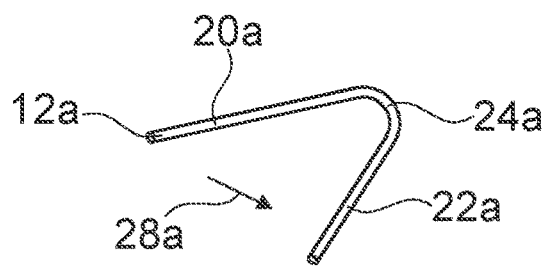
Figure 5A:
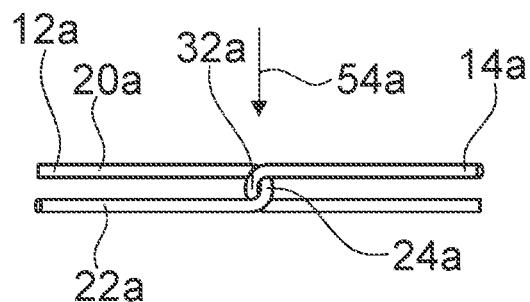
Figure 5B:
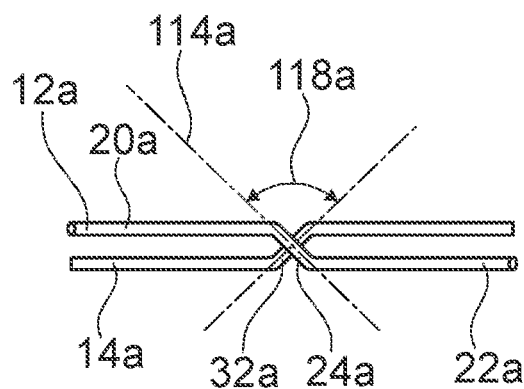
Figure 5C:
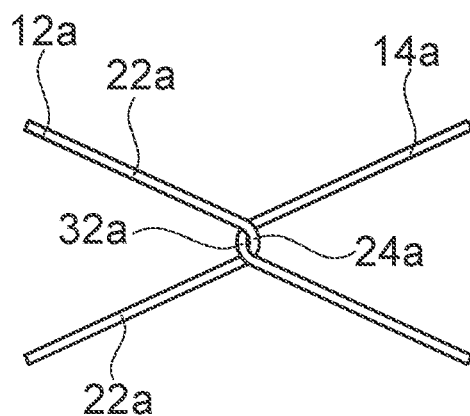
Figure 5D:
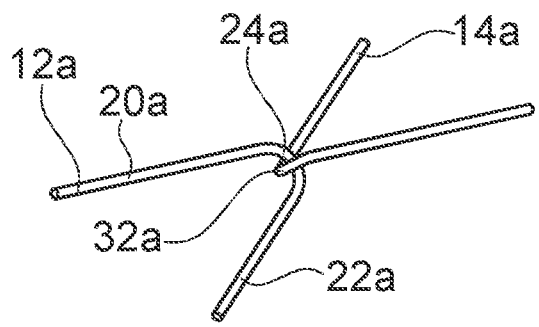

The first leg 20*a* follows at least section-wise a straight contour. In the present case the first leg 20*a* follows a straight contour. The second leg 22*a* follows at least section-wise a straight contour. In the present case the second leg 22*a* follows a straight contour. The first leg 20*a* and/or the second leg 22*a* are free of a curvature and/or bend and/or kink. The bending region 24*a* has a contour describing, in a longitudinal view, in parallel to the longitudinal direction 28*a* of the helix 12*a*, a 180° bend. In FIG. 4*a* the helix 12*a* is shown in a longitudinal view.

The first leg 20*a* extends at least section-wise, in particular entirely, in a first plane and the second leg 22*a* extends at least section-wise, in particular entirely, in a second plane that is parallel to the first plane. In the longitudinal view, the first leg 20*a* extends in parallel to the second leg 22*a*.

The further helix 14*a* comprises a further bending region 32*a*. The bending region 24*a* and the further bending region 32*a* are connected. The bending region 24*a* and the further bending region 32*a* implement a connecting point of the first helix 12*a* and the further helix 14*a*.

FIG. 5 shows a portion of the wire netting 10*a*, which comprises the bending region 24*a* and the further bending region 32*a*, in different views. FIG. 5*a* shows a view in a longitudinal direction 28*a* of the helix 12*a*. FIG. 5*b* shows the portion of the wire netting 10*a* in a transverse view perpendicularly to the longitudinal direction 28*a* of the helix 12*a* in the main extension plane of the helix 12*a*. FIG. 5*c* shows a view in the frontal direction 54*a*. FIG. 5*d* shows a perspective view.

The helix 12*a* and the further helix 14*a* intersect in a proximity of the further bending region 32*a* at least substantially perpendicularly. In the transverse view, the bending region 24*a* and the further bending region 32*a* include an intersection angle 118*a*. The intersection angle 118*a* depends on the second gradient angle 30*a* and a correspondingly defined further second gradient angle of the further helix 14*a*. In the present case, the intersection angle 118*a* is 90°.

For other first gradient angles a second gradient angle of 45° is advantageously chosen in such a way that accordingly implemented helices intersect perpendicularly in connecting points and said connecting points advantageously have a high mechanical load-bearing capacity.

FIG. 6 shows the helix 12*a*, viewed in a longitudinal direction 28*a* of the helix 12*a*, in a schematic representation. In FIGS. 1 to 5 the helix 12*a*, in particular the bending region 24*a*, is shown in a representation that is simplified with respect to the representation in FIG. 6. In the longitudinal view in parallel to the longitudinal direction 28*a* of the helix 12*a*, the bending region 24*a* comprises a bending zone 34*a* with a bending curvature and with a first transition zone 36*a* which is connected to the first leg 20*a* and has a first transition curvature differing from the bending curvature. The bending zone 34*a* is connected to the first transition zone 36*a*. The bending zone 34*a* and the first transition zone 36*a* are arranged directly side by side and in particular merge into one another. The bending zone 34*a* and the first transition zone 36*a* are connected to one another in a one-part implementation. The first transition zone 36*a* merges into the first leg 20*a*. The first transition zone 36*a* is connected to the first leg 20*a* in a one-part implementation.

In the longitudinal view, the bending region 24*a* comprises a second transition zone 38*a* which is connected to the second leg 22*a* and has a second transition curvature that differs from the bending curvature. The second transition zone 38*a* is connected to the bending zone 34*a* in a one-part implementation. The second transition zone 38*a* merges into the second leg 22*a*. The second transition zone 38*a* is connected to the second leg 22*a* in a one-part implementation. The bending zone 34*a*, the first transition zone 36*a* and the second transition zone 38*a* together embody the bending region 24*a*.

The first transition curvature and the second transition curvature are identical. It is however also conceivable that a first transition curvature and a second transition curvature are different from one another, allowing to create, for example, a wire netting with a front side and a rear side, which differ in particular regarding their spring characteristic curves and/or deformation characteristics.

In the longitudinal view the first transition zone 36*a* and the second transition zone 38*a* are embodied mirror-symmetrically. The first transition zone 36*a* and the second transition zone 38*a* are mirror-symmetrical with respect to a main extension plane of the wire netting 10*a*. The first transition zone 36*a* and the second transition zone 38*a* are mirror-symmetrical with respect to a plane that extends centrally between the plane in which the first leg 20*a* extends and the plane in which the second leg 22*a* extends and which is parallel to the plane in which the first leg 20*a* extends, the centrally-extending plane being parallel to said planes.

The bending curvature is greater than the first transition curvature. The bending curvature is greater than the second transition curvature. The bending zone 34*a* follows a circle-shaped course. In the longitudinal view, the bending zone 34*a* is bent in a circular-arc shape. In the longitudinal view, the bending zone 34*a* is bent by less than 180°. The bending zone 34*a*, the first transition zone 36*a* and the second transition zone 38*a* are, in the longitudinal view, all bent by 180°. In the present case, the bending curvature, in particular the contour of the bending zone 34*a*, merges into the first transition curvature, in particular into a contour of the first transition zone 36a, continuously, in particular mathematically continuously, in particular kink-free. Furthermore, in the present case, the bending curvature, in particular the contour of the bending zone 34a, merges into the second transition curvature, in particular into a contour of the second transition zone 38a, continuously, in particular mathematically continuously, in particular kink-free. Moreover, in the present case the first transition curvature, in particular the course of the first transition zone 36a, merges into the straight contour of the first leg 20a continuously, in particular mathematically continuously, in particular kink-free. Moreover, in the present case the second transition curvature, in particular the contour of the second transition zone 38a, merges into the straight contour of the second leg 22a continuously, in particular mathematically continuously, in particular kink-free. It is also conceivable that respective transitions are provided with a kink. It is further conceivable that a first transition curvature and/or a second transition curvature disappears, wherein in particular a first transition zone and/or a second transition zone have a straight contour at least section-wise or over their entire extension.

FIG. 7 shows a bend test device 120a for carrying out a reverse bend test, in a schematic view. The bend test device 120a comprises clamping jaws 122a, 124a, which are configured to clamp a test piece of a wire between them. In the case shown it is a test piece 42a of the wire 18a. The bend test device 120a comprises a bending lever 128a, which is supported in such a way that it is pivotable to-and-fro-wise. The bending lever 128a comprises drivers 130a, 132a for the test piece 42a of the wire 18a. The bend test device 120a comprises a bending cylinder 40a, about which the test piece 42a of the wire 18a is bent in the reverse bend test. The bend test device 120a comprises a further bending cylinder 126a, which is embodied identically to the bending cylinder 40a. The further bending cylinder 126a is arranged opposite the bending cylinder 40a. In the reverse bend test the bending lever 128a bends the test piece 42a of the wire 18a alternatingly about the bending cylinder 40a and the further bending cylinder 126a by 90° respectively. The reverse bend test is usually carried out until the test piece 42a of the wire 18a breaks, for the purpose of testing a load-bearing capacity and/or flexibility of said test piece 42a of the wire 18a.

The bending cylinder 40a has a diameter of maximally 2d, i.e. no more than twice the diameter d of the wire. In the present case, the bending cylinder 40a has a diameter of 5 mm. Advantageously, a bending cylinder diameter of 3.75 mm is chosen for a wire diameter of 2 mm. Advantageously, a bending cylinder diameter of 5 mm is chosen for a wire diameter of 3 mm. Advantageously, a bending cylinder diameter of 7.5 mm is chosen for a wire diameter of 4 mm. Advantageously, a bending cylinder diameter of 10 mm is chosen for a wire diameter of 5 mm.

The test piece 42a of the wire 18a has in the present case a length of approximately 85 mm. Advantageously, a test piece length of approximately 75 mm is chosen for a wire diameter of 2 mm. Advantageously, a test piece length of approximately 85 mm is chosen for a wire diameter of 3 mm. Advantageously, a test piece length of approximately 100 mm is chosen for a wire diameter of 4 mm. Advantageously, a test piece length of approximately 115 mm is chosen for a wire diameter of 5 mm. Preferably the test piece 42a is cut off the wire 18a, in particular prior to a manufacturing of the longitudinal element 16a and/or of the wire netting 10a.

In the reverse bend test about the bending cylinder 40a and in particular about the further bending cylinder 126a, the wire 18a, respectively the test piece 42a of the wire 18a, is bendable by at least 90° in opposite directions at least M times without breaking, wherein M may be determined, if applicable by rounding down, to be $C \cdot R^{-0.5} \cdot d^{-0.5}$, and wherein d is the diameter of the wire 18a in mm, R is the tensile strength of the wire 18a in N mm$^{-2}$ and C is a factor of at least 400 N$^{0.5}$ mm$^{0.5}$. The reverse bend test permits testing the wire 18a, in addition to its tensile strength, also regarding its flexural characteristics, which are relevant both for a manufacturing of the wire netting 10a as well as for a deformation behavior of the wire netting 10a in an installation and in particular in case of an impact. If a greater value is chosen for C, wires may be chosen which have a higher flexibility, e.g. for more demanding applications. C may, for example, be a factor of 500 N$^{0.5}$ mm$^{0.5}$ or 750 N$^{0.5}$ mm$^{0.5}$ or 1000 N$^{0.5}$ mm$^{0.5}$ or 2000 N$^{0.5}$ mm$^{0.5}$ or even greater. In the present case, the above formula gives a value of $$M'=400 \quad N^{0.5} \quad mm^{0.5} \times (1770 \quad N \quad mm^2)^{-0.5} \times (3 \ mm)^{-0.5}=5.4892.$$

In the present case, applying this formula and then rounding down M', results in M having a value of 5.

The bend test device 120a defines a bending length 133a. The bending length 133a is a vertical distance between a highest point of the bending cylinder 40a and a lowest point of the drivers 130a, 132a. In the present case, the bending length 133a is approximately 35 mm. Advantageously a bending length of approximately 25 mm is chosen for a wire diameter of 2 mm. Advantageously a bending length of approximately 35 mm is chosen for a wire diameter of 3 mm. Advantageously a bending length of approximately 50 mm is chosen for a wire diameter of 4 mm. Advantageously a bending length of approximately 75 mm is chosen for a wire diameter of 5 mm.

By way of the reverse bend test, a suitable wire 18a may be identified prior to a manufacturing of the wire netting 10a. The wire 18a is herein identified as suitable if the test piece 42a of the wire 18a is bendable to and fro about the bending cylinder 40a and in particular about the further bending cylinder 126a by at least 90° in opposite directions at least M times without breaking.

FIG. 8 shows a pressing device 134a for the purpose of executing a press test, in a schematic representation. The pressing device 134a comprises two opposite parallel plates 48a, 50a, namely a first plate 48a and a second plate 50a. The plates 48a, 50a are movable toward each other along a press path 52a. In the present case the first plate 48a is movable toward the second plate 50a. Furthermore, in the present case the plates 48a, 50a are moved toward each other in the press test with a velocity of approximately 117 μm s$^{-1}$. Advantageously, prior to the press test the first plate 48a and/or the second plate 50a is first of all traversed towards contacting the test piece 42a of the wire 18a, in particular with a pre-load of approximately 10 kN and/or with a velocity of approximately 333 μm s$^{-1}$, wherein other pre-loads and/or velocities, e.g. differing by a factor 2, a factor 5, a factor 10, a factor 20, a factor 50, a factor 100, are also conceivable.

The press test comprises pressing a test piece 46a of the helix 12a. The test piece 46a of the helix 12a is taken from the helix 12a, in particular cut out of the helix 12a. The test piece 46a of the helix 12a comprises, in particular precisely, five legs and four bending regions. The helix 12a has a transverse extension 44a (cf. also FIG. 4a). In the present case the transverse extension 44a is approximately 12 mm. The transverse extension 44a depends on a geometry of the bending region 24a. The transverse extension 44a depends on the bending curvature, the first transition curvature and the second transition curvature. Any other transverse extensions, and their adaptions to an application, are conceivable. For example, smaller transverse extensions may be applied if a wire netting having a small thickness is required, e.g. a transverse extension of maximally 10 mm or maximally 7 mm. Greater transverse extensions are also conceivable, e.g. a transverse extension of more than 15 mm or more than 25 mm or more than 40 mm or even more. It is in particular conceivable, in case of greater diameters of longitudinal elements, to choose correspondingly greater transverse extensions. However, closely bent wire nettings are also conceivable, having a small transverse extension at the same time as a great diameter of a corresponding longitudinal element. In particular for the purpose of realizing small netting thicknesses, it is conceivable that a first bending region and a second bending region intersect including a small angle, wherein in particular a corresponding second gradient angle has a value that is considerably below 45°, e.g. 30° or 20° or even less. It is also conceivable that a first bending region and a second bending region intersect including a large angle, wherein a corresponding second gradient angle has a value that is considerably above 45°, e.g. an angle of 60° or 70° or even more, as a result of which in particular a wire netting is realizable featuring a great thickness and narrowly implemented connecting points between helices.

FIG. 9 shows a spring characteristic curve 56a of the test piece 46a of the helix 12a in the press test in a schematic press path force diagram 58a. The press path force diagram 58a comprises a press path axis 136a, on which a position of the plates 48a, 50a, in particular of the first plate 48a, is marked along the press path 52a. The press path force diagram 58a comprises a force axis 138a, on which a press force occurring in the press test is marked in a respective point of the press path 52a. The pressing device 134a is configured to determine the spring characteristic curve 56a according to the press path force diagram 58a. The test piece 46a of the helix 12a, taken from the helix 12a, shows in the press test between the parallel plates 48a, 50a—the press test comprising a pressing via moving the plates 48a, 50a along the press path 52a in parallel to the frontal direction 54a of the helix 12a—the spring characteristic curve 56a, which in the press path force diagram 58a has a first partial characteristic curve 60a starting from a start of the press path 52a and running at least approximately linearly, with a first gradient. In the present case the first partial characteristic curve 60a runs linearly.

The press path 52a herein starts with the plates 48a, 50a abutting on the test piece 46a of the helix 12a, wherein no press force acts onto the test piece 46a of the helix 12a yet. The press path 52a then extends up to a point in which the test piece 46a of the helix 12a is flattened. In particular, the press path 52a extends over a distance that is approximately equivalent to a difference between the transverse extension 44a and the wire diameter d. In particular, the test piece 46a of the helix 12a is flattened in the press test at least substantially down to the wire diameter d.

The first partial characteristic curve 60a extends over a press path value range 66a, which is equivalent at least to a quarter of the transverse extension 44a of the helix 12a.

The first partial characteristic curve 60a is directly followed by an approximately linearly extending second partial characteristic curve 62a. The second partial characteristic curve 62a has a second gradient, which is greater than the first gradient. The second gradient is no more than four times as great as the first gradient. In the present case the second gradient is approximately twice as great as the first gradient. However, other factors between the first gradient and the second gradient are also conceivable, e.g. 1.1 or 1.5 or 2.5 or 3 or 3.5 or the like.

The spring characteristic curve 56a has a kink 70a in a transition region 68a between the first partial characteristic curve 60a and the second partial characteristic curve 62a. The kink 70a corresponds to a jump-wise change of a gradient of the spring characteristic curve 56a from the first gradient to the second gradient.

The second partial characteristic curve 62a runs over a press path value range 72a, which corresponds to at least a fifth of the transverse extension 44a of the helix 12a.

The second partial characteristic curve 62a is followed by a convexly curved third partial characteristic curve 64a. The third partial characteristic curve 64a has a continuously increasing gradient. A transition between the second partial characteristic curve 62a and the third characteristic 64a is free of a kink. The second gradient continuously merges into the gradient of the third partial characteristic curve 64a. In a transition point 116a between the second partial characteristic curve 62a and the third partial characteristic curve 64a, the gradient of the third partial characteristic curve 64a corresponds to the second gradient.

FIG. 10 shows a bending device 74a for producing the wire netting 10a, in a perspective view. FIG. 11 shows a bending space 140a of the bending device 74a in a first operating state, in a perspective view. FIG. 12 shows the bending space 140a in a second operating state, in a perspective view. The bending device 74a is configured for producing the wire netting 10a. The bending device 74a is configured for producing the helix 12a. The bending device 74a is configured for a bending of the helix 12a according to the geometry of the helix 12a, in particular of the legs 20a, 22a and of the bending region 24a of the helix 12a. The bending device 74a is configured for producing the wire netting 10a, respectively the helix 12a, from a helix blank 76a. The helix blank 76a is herein implemented by the longitudinal element 16a in a non-bent state. In the present case the wire 18a implements the helix blank 76a. It is however also conceivable that a helix blank is implemented as a wire bundle and/or a wire strand and/or a wire rope and/or another type of a longitudinal element. The bending device 74a is configured to produce the helix 12a by a bending of the helix blank 76a.

The bending device 74a comprises a bending unit 78a. The bending unit 78a comprises a bending mandrel 80a as well as a bending table 82a. The bending table 82a is configured for a bending of the helix blank 76a about the bending mandrel 80a. The bending table 82a is supported in a manner completely circulating the bending mandrel 80a. In manufacturing, the bending table 82a runs about the bending mandrel 80a continuously in a circulation direction 142a. The bending mandrel 80a has a longitudinal axis 144a. The longitudinal axis 144a of the bending mandrel 80a extends in parallel to a main extension direction 94a of the bending mandrel 80a.

The bending device 74a comprises a feed unit 84a, which is configured for forward-feeding of the helix blank 76a in a feed direction 88a along a feed axis 86a. The feed axis 86a is arranged in parallel to the feed direction 88a. The feed direction 88a extends in parallel to a main extension direction of the helix blank 76a. The feed axis 86a and the longitudinal axis 144a of the bending mandrel 80a include an angle that is at least substantially and in particularly exactly equivalent to the first gradient angle 26a. The first gradient angle 26a is adjustable by way of an adjustment of the feed axis 86a with respect to the longitudinal axis 144a of the bending mandrel 80a.

The bending device 74a comprises a geometry adjusting unit 90a, which is configured to adjust a geometry of the helix 12a. The geometry adjusting unit 90a is configured to adjust a length of the first leg 20a and of the second leg 22a. The geometry adjusting unit 90a is configured to adjust the transverse extension 44a of the helix 12a. The geometry adjusting unit 90a is configured to adjust the first gradient angle 26a. The geometry adjusting unit 90a is configured to adjust the second gradient angle 30a. The geometry adjusting unit 90a is configured to adjust the bending curvature. The geometry adjusting unit 90a is configured to adjust the first transition curvature. The geometry adjusting unit 90a is configured to adjust the second transition curvature. The geometry adjusting unit 90a is configured to adjust the geometry of the bending region 24a, in particular of the bending zone 34a, in particular of the first transition zone 36a and in particular of the second transition zone 38a. The geometry adjusting unit 90a comprises an orientation element 146a for adjusting the angle between the feed axis 86a and the longitudinal axis 144a of the bending mandrel 80a. The orientation element 146a is embodied as an oblong hole.

During manufacturing the helix blank 76a is fed forward repeatedly. Following an executed forward-feeding, the bending unit 78a, in particular the bending table 82a, respectively bends the helix blank 76a about the bending mandrel 80a to generate a bending region 24a of the manufactured helix 12a. A diameter of the bending mandrel 80a herein defines the bending curvature of the bending zone 34a and at least partly defines the transverse extension 44a of the helix 12a. In particular, the diameter of the bending mandrel 80a defines an inner radius of the bending region 24a.

The geometry adjusting unit 90a comprises a transverse stroke unit 92a, which is configured for changing a position of the bending table 82a with respect to the feed axis 86a, along the main extension direction 94a of the bending mandrel 80a periodically and in a manner synchronized to a circulation of the bending table 82a about the bending mandrel 80a. In the present case the transverse stroke unit 92a comprises a conveying element 148a, which conveys the helix blank 76a to the bending table 82a. The conveying element 148a is embodied as a guiding table 150a with guiding rolls 152a, 154a. The conveying element 148a is supported displaceably, with respect to the bending table 82a, in a transverse stroke direction 156a and counter to said transverse stroke direction 156a. The transverse stroke direction 156a runs in parallel to the main extension direction 94a of the bending mandrel 80a. The geometry adjusting unit 90a is configured for adjusting a maximum transverse stroke 160a. The conveying element 148a is displaceable, by the maximum transverse stroke 160a, in parallel to the transverse stroke direction 156a.

The transverse stroke unit 92a comprises a coupling element 162a which mechanically couples a movement of the conveying element 148a to the circulation of the bending table 82a about the bending mandrel 80a. In the present case the coupling element 162a is a lever drive mechanically coupling the conveying element 148a to a shared drive (not shown) of the bending device 74a. During a circulation of the bending table 82a about the bending mandrel 80a, the conveying element 148a is deflected, parallel to the transverse stroke direction 156a, out of a start position and away from the bending table 82a. Especially advantageously, in this circulation of the bending table 82a, the conveying element 148a is then moved back into its start position. In particular, the transverse stroke unit 92a is configured to provide a bending region generated by bending with the second gradient angle 30a. In particular, the transverse stroke unit 92a is configured to generate an adjustable maximum transverse stroke 160a. By the maximum transverse stroke 160a the second gradient angle 30a is adjustable. The maximum transverse stroke 160a allows generating a second gradient angle 30a, which differs from the first gradient angle 26a, in particular by way of the helix blank 76a being laterally offset in a bending of a bending region about the bending mandrel 80a.

In the present case the bending mandrel 80a is driven. The bending mandrel 80a is supported rotatably about its longitudinal axis 144a. The bending mandrel 80a is coupled with the shared drive of the bending device 74a via a belt 164a. The bending mandrel 80a is embodied adjustable. The bending unit 78a is loadable with bending mandrels of differing diameters.

The geometry adjusting unit 90a comprises an abutment unit 96a with at least one abutment element 98a defining a maximum feed-forward position for the helix blank 76a. In a forward feeding the helix blank 76a may be fed forward by the feed unit 84a maximally up to the maxim feed-forward position. Prior to being bent about the bending mandrel 80a by the bending table 82a, the helix blank 76a is situated in the maximum feed-forward position. In the maximum feed-forward position, the helix blank 76a abuts on the abutment element 98a with a most recently bent bending region 166a of the helix 12a. The first operating state shown in FIG. 11 corresponds to a situation directly before the bending of the helix blank 76a about the bending mandrel 80a. In the first operating state, the helix blank 76a is in the maximum feed-forward position. The second operating state shown in FIG. 12 corresponds to a situation during the bending of the helix blank 76a about the bending mandrel 80a. The bending table 82a is in the second operating state offset, along the circulation direction 142a, relative to its position in the first operating state.

The abutment element 98a is supported in a manner fully circulating about the bending mandrel 80a. In manufacturing, the abutment element 98a continuously circulates about the bending mandrel 80a in the circulation direction 142a.

In the circulation of the bending table 82a about the bending mandrel 80a, a position of the bending table 82a with respect to the abutment element 98a is variable. The bending table 82a is supported pivotally about a pivot axis 102a which, during the circulation of the bending table 82a about the bending mandrel 80a, itself circulates about the bending mandrel 80a, in particular in the circulation direction 142a. In manufacturing, the pivot axis 102a moves on a circular path 168a (cf. FIG. 13). In manufacturing, the pivot axis 102a moves with a constant angular velocity. During bending the bending table 82a and the abutment element 98a circulate about the bending mandrel 80a with equivalent velocities. Following the bending, the bending table 82a pivots about the pivot axis 102a, as a result of which a maximum bending angle is defined. Then, in particular during the forward-feeding of the helix blank 76a, the bending table 82a pivots back about the pivot axis 102a. In the first operating state the abutment element 98a lies upon the bending table 82a.

The abutment element 98a comprises a concavely curved abutment surface 100a. In the circulation direction 142a, the abutment surface 100a is curved in a circular-arc shape accordingly. The abutment surface 100a is moreover curved in a circular-arc shape perpendicularly to the curvature in the circulation direction 142a. A curvature radius, which is perpendicular to the circulation direction 142a, at least substantially corresponds to a curvature radius of the bending region 24a. In the maximum feed-forward position, the most recently bent bending region 166a abuts on the abutment surface 100a, which curves about the most recently bent bending region 166a in a circular-arc shape.

In a feed-forward operating state, in which the forward-feeding of the helix blank 76a is effected, a position of the abutment element 98a with respect to the feed axis 86a is variable. In the feed-forward operating state, in particular following the helix blank 76a abutting on the abutment element 98a and being thus, in particular, in the maximum feed-forward position, the abutment element 98a moves along the most recently bent bending region 166a in the circulation direction 142a.

The bending unit 78a is configured for a bending of a helix blank with at least one wire made of a high-tensile steel. In the present case the helix blank 76a is bendable by means of the bending unit 78a. The bending unit 78a is further configured for bending helix blanks implemented of different longitudinal elements, e.g. of wire strands, wire ropes, wire bundles or the like, as well as of single wires, respectively in particular having different diameters and/or tensile strengths, into helices. Moreover the bending device 74a is configured for manufacturing a wire netting, in particular the wire netting 10a, from correspondingly bent helices.

The bending unit is configured for bending the helix blank 76a in a single circulation, in particular in each circulation, of the bending table 82a about the bending mandrel 80a by more than 180°. A bending angle is herein defined by a point in time of a pivoting of the bending table 82a about the pivot axis 102a. The bending unit 78a is configured to overbend the helix blank 76a, in particular to compensate for a rebound of the helix blank 76a after bending, due to its high degree of hardness. The bending unit 78a is configured to provide the bending region 24a with a total angle of precisely 180°, allowing the helix 12a being manufactured extending straight in itself.

The geometry adjusting unit 90a comprises a holding unit 104a with a holding element 106a which, during the bending about the bending mandrel 80a, at least partly fixates the helix 12a, viewed from the bending mandrel 80a, behind the bending table 82a. The holding element 106a partly engages around the helix 12a. The holding element 106a is embodied fork-like. During a bending of the helix blank 76a about the bending mandrel 80a, wherein the helix 12a is co-rotated in the circulation direction 142a, the holding element 106a supports the helix 12a.

The holding element 106a is supported in a manner completely circulating about the bending mandrel 80a. The holding element 106a is supported pivotally about a pivot axis 108a, which itself circulates about the bending mandrel 80a during a circulation of the holding element 106a about the bending mandrel 80a. The holding element 106a is supported on the bending table 82a. The pivot axis 108a of the holding element 106a is identical to the pivot axis 102a of the bending table 82a. The pivot axis 108a extends through a support pin 170a supporting the holding element 106a on the bending table 82a. In a circulation of the holding element 106a about the bending mandrel 80a, a position of the holding element 106a with respect to the bending table 82a is variable. After bending the holding element 106a is pivoted away from the helix 12a and is moved back into a start position underneath the helix 12a. Then the holding element 106a engages around the helix 12a engages around the helix 12a in a proximity of another leg than before.

FIG. 13 shows slotted links 172a, 174a of the bending table 82a and of the holding element 106a, in a schematic side view. A first slotted link 172a effects a pivoting of the bending table 82a about the pivot axis 102a in the circulation of the bending table 82a about the bending mandrel 80a. A second slotted link 174a effects a pivoting of the holding element 106a about the pivot axis 108a of the holding element 106a in the circulation of the holding element 106a about the bending mandrel 80a.

FIG. 14 shows a schematic flow chart of a method for producing the wire netting 10a. In a first method step 176a, a test piece 42a of the wire 18a is taken from the longitudinal element 16a and, by carrying out the already described reverse bend test, the wire 18a is identified as suitable. Accordingly, a non-suitable wire would not be used further on. In a second method step 178a, the wire netting 10a is manufactured from the longitudinal element 16a with the wire 18a identified as suitable. The wire netting 10a is manufactured by bending, wherein the helix 12a is produced. In the second method step 178a, the helix 12a is produced via the bending device 74a. In a third method step 180a, a test piece 46a of the helix 12a is taken from the helix 12a and is tested via the press test already described. The third method step 180a may be effected following a short test run of manufacturing a test piece of the wire netting 10a and/or for quality control purposes.

The method steps 176a, 178a, 180a described may also be carried out independently from one another. It is, for example, conceivable to process a wire or a corresponding longitudinal element, which has been identified as suitable by the reverse bend test, to implement a wire netting in a different manner. It is moreover conceivable to manufacture via the bending device a wire netting that does not comprise a wire showing the described behavior in the reverse bend test and/or in the press test. Furthermore any manufacturing method is conceivable for a wire netting in particular showing the described behavior in the press test. It is principally conceivable to manufacture a wire netting having one or a plurality of the features described by means of a braiding knife and/or by means of a bending table that is pivotable to and fro and/or by means of another suitable manufacturing device.

FIGS. 15 to 25 show nine further exemplary embodiments of the invention. The following description and the drawings are restricted substantially to the differences between the exemplary embodiments wherein, as regards identically designated structural components, in particular as regards structural components with the same reference numerals, principally the drawings and/or the description of the other exemplary embodiments, in particular of FIGS. 1 to 14, may also be referred to. For the purpose of distinguishing the exemplary embodiments, the letter a has been added to the reference numerals of the exemplary embodiment in FIGS. 1 to 14. In the exemplary embodiments of FIGS. 15 to 25, the letter a has been substituted by the letters b to j.

FIG. 15 shows a second wire netting 10b in a schematic front view. The second wire netting 10b comprises a plurality of helices 12b, which are braided with one another and at least one helix 12b of which is manufactured of a longitudinal element 16b with a wire 18b. The longitudinal element 16b is in the present case embodied as a wire bundle with the wire 18b. The helix 12b comprises a first leg 20b, a second leg 22b and a bending region 24b connecting the first leg 20b and the second leg 22b. In a front view perpendicularly to a main extension plane of the helix 12b, the first leg 20b extends with a first gradient angle 26b with respect to a longitudinal direction 28b of the helix 12b.

FIG. 16 shows the bending region 24b of the helix 12b in a transverse view parallel to the main extension plane of the helix 12b and perpendicularly to the longitudinal direction 28b of the helix 12b. In the transverse view the bending region 24b at least section-wise extends with a second gradient angle 30b with respect to the longitudinal direction 28b of the helix 12b, which differs from the first gradient angle 26b.

In the present case the first gradient angle 26b is smaller than 45°. The first gradient angle 26b is approximately 30°. Due to the small first gradient angle 26b, the second wire netting 10b features wide meshes. The second wire netting 10b is configured to be rolled out transversely to a slope, in such a way that it is possible to lay out the second wire netting 10b transversely to the slope without interruptions over a large distance. In parallel to the slope, a height of such an installation is hence equivalent to a width of the second wire netting 10b, respectively to a length of the helix 12b.

The second gradient angle 30b is greater than the first gradient angle 26b. In the present case the second gradient angle 30b is approximately 45°. FIG. 17 shows a third wire netting 10c in a schematic front view. The third wire netting 10c comprises a plurality of helices 12c, which are braided with one another and at least one helix 12c of which is manufactured of a longitudinal element 16c with a wire 18c. The longitudinal element 16c is in the present case embodied as a wire strand with the wire 18c. The longitudinal element 16c comprises a plurality of wires 18c which are wound around one another and are embodied identically. The helix 12c comprises a first leg 20c, a second leg 22c and a bending region 24c connecting the first leg 20c and the second leg 22c. In a front view perpendicularly to a main extension plane of the helix 12c, the first leg 20c extends with a first gradient angle 26c with respect to a longitudinal direction 28c of the helix 12c.

FIG. 18 shows the bending region 24c of the helix 12c in a transverse view parallel to the main extension plane of the helix 12c and perpendicularly to the longitudinal direction 28c of the helix 12c. In the transverse view the bending region 24c at least section-wise extends with a second gradient angle 30c with respect to the longitudinal direction 28c of the helix 12c, which differs from the first gradient angle 26c.

In the present case the first gradient angle 26c is larger than 45°. The first gradient angle 26c is approximately 75°. Due to the large first gradient angle 26c, the third wire netting 10c features narrow meshes. The wire netting 10c has hence a high tensile strength in a longitudinal direction of the meshes. The wire netting 10c is furthermore easier to stretch in a transverse direction of the meshes than in the longitudinal direction.

The second gradient angle 30c is smaller than the first gradient angle 26c. In the present case the second gradient angle 30c is approximately 45°.

FIG. 19 shows a helix 12d of a fourth wire netting, viewed in a longitudinal direction of the helix 12d, in a schematic view. The helix 12d is manufactured of a longitudinal element 16d with at least one wire 18d. The helix 12d comprises a first leg 20d, a second leg 22d and a bending region 24d connecting the first leg 20d and the second leg 22d. In a longitudinal view in parallel to a longitudinal direction 28d of the helix 12d, the bending region 24d comprises a bending zone 34d with a bending curvature. In the longitudinal view the bending region 24d furthermore comprises a first transition zone 36d, which is connected to the first leg 20d, with a first transition curvature differing from the bending curvature. Moreover, in the longitudinal view the bending region 24d comprises a second transition zone 38d, which is connected to the second leg 22d, with a second transition curvature.

The first leg 20d features a curved contour. The first leg 20d is free of a straight contour. The bending zone 34d is curved in a circular-arc shape. The first transition curvature and the second transition curvature are identical.

FIG. 20 shows a helix 12e of a fifth wire netting, viewed in a longitudinal direction of the helix 12e, in a schematic view. The helix 12e is manufactured of a longitudinal element 16e with at least one wire 18e. The helix 12e features a first leg 20e, a second leg 22e and a bending region 24e connecting the first leg 20e and the second leg 22e. In a longitudinal view, the bending region 24e comprises a bending zone 34e with a bending curvature. Furthermore, in the longitudinal view parallel to a longitudinal direction 28e of the helix 12e, the bending region 24e comprises a first transition zone 36e, which is connected to the first leg 20e, with a first transition curvature differing from the bending curvature. Moreover, in the longitudinal view the bending region 24e comprises a second transition zone 38e, which is connected to the second leg 22e, with a second transition curvature.

The first transition zone 36e section-wise follows a straight contour. The first transition zone 36e implements a portion of the first leg 20e. In the present case the first transition zone 36e implements half of the first leg 20e. The first transition zone 36e continuously merges into the first leg 20e. Analogously the second transition zone 38e implements half of the second leg 22e.

FIG. 21 shows a spring characteristic curve 56f of a test piece of a helix of a sixth wire netting, in a schematic press path force diagram 58f. The spring characteristic curve 56f was created, analogously to the spring characteristic curve 56a in the exemplary embodiment of FIGS. 1 to 14, by pressing the test piece of the helix along a press path. The sixth wire netting is manufactured from a high-tensile steel wire with a wire diameter of 2 mm. The sixth wire netting features a leg length of approximately 65 mm.

The spring characteristic curve 56f comprises, starting from a start of the press path, a first partial characteristic curve 60f extending approximately linearly and having a first gradient. The first partial characteristic curve 60f is followed by a second partial characteristic curve 62f extending approximately linearly and having a second gradient, which is greater than the first gradient. In a transition region 68f between the first partial characteristic curve 60f and the second partial characteristic curve 62f, the spring characteristic curve 56f has a kink 70f.

The second partial characteristic curve 62f is followed by a convexly curved third partial characteristic curve 64f. A transition between the second partial characteristic curve 62f and the third partial characteristic curve 64f is free of a kink.

FIG. 22 shows a spring characteristic curve 56g of a test piece of a helix of a seventh wire netting, in a schematic press path force diagram 58g. The spring characteristic curve 56g was obtained, analogously to the spring characteristic curve 56a in the exemplary embodiment of FIGS. 1 to 14, via pressing the test piece of the helix along a press path. The seventh wire netting is manufactured of a high-tensile steel wire with a wire diameter of 2 mm. The seventh wire netting has a leg length of approximately 45 mm.

The spring characteristic curve 56g comprises, starting from a start of the press path, a first partial characteristic curve 60g extending approximately linearly and having a first gradient. The first partial characteristic curve 60g is followed by a second partial characteristic curve 62g, which extends approximately linearly and has a second gradient that is greater than the first gradient. In a transition region 68g between the first partial characteristic curve 60g and the second partial characteristic curve 62g, the spring characteristic curve 56g has a kink 70g.

The second partial characteristic curve 62g is followed by a convexly curved third partial characteristic curve 64g. A transition between the second partial characteristic curve 62g and the third partial characteristic curve 64g is free of a kink.

FIG. 23 shows a spring characteristic curve 56h of a test piece of a helix of an eighth wire netting, in a schematic press path force diagram 58h. The spring characteristic curve 56h was obtained, analogously to the spring characteristic curve 56a in the exemplary embodiment of FIGS. 1 to 14, by pressing the test piece of the helix along a press path. The eighth wire netting is manufactured of a high-tensile steel wire with a wire diameter of 3 mm. The eighth wire netting features a leg length of approximately 65 mm.

Starting from a start of the press path, the spring characteristic curve 56h comprises a first partial characteristic curve 60h extending approximately linearly with a first gradient. The first partial characteristic curve 60h is followed by a second partial characteristic curve 62h extending approximately linearly with a second gradient, which is greater than the first gradient. In a transition region 68h between the first partial characteristic curve 60h and the second partial characteristic curve 62h the spring characteristic curve 56h has a kink 70h.

The second partial characteristic curve 62h is followed by a convexly curved third partial characteristic curve 64h. A transition between the second partial characteristic curve 62h and the third partial characteristic curve 64h is free of a kink.

FIG. 24 shows a spring characteristic curve 56i of a test piece of a helix of a ninth wire netting, in a schematic press path force diagram 58i. The spring characteristic curve 56i was obtained, analogously to the spring characteristic curve 56a in the exemplary embodiment of FIGS. 1 to 14, by pressing the test piece of the helix along a press path. The ninth wire netting is manufactured of a high-tensile steel wire with a wire diameter of 4 mm. The ninth wire netting features a leg length of approximately 80 mm.

Starting from a start of the press path, the spring characteristic curve 56i comprises a first partial characteristic curve 60i with a first gradient. The first partial characteristic curve 60i is followed by a second partial characteristic curve 62i extending approximately linearly, with a second gradient which is greater than the first gradient. In a transition region 68i between the first partial characteristic curve 60i and the second partial characteristic curve 62i, the spring characteristic curve 56i has a kink 70i.

The second partial characteristic curve 62i is followed by a convexly curved third partial characteristic curve 64i. A transition between the second partial characteristic curve 62i and the third partial characteristic curve 64i is free of a kink.

FIG. 25 shows a spring characteristic curve 56j of a test piece of a helix of a tenth wire netting, in a schematic press path force diagram 58j. The spring characteristic curve 56j was obtained, analogously to the spring characteristic curve 56a in the exemplary embodiment of FIGS. 1 to 14, by pressing the test piece of the helix along a press path. The tenth wire netting is manufactured from a high-tensile steel wire with a wire diameter of 4 mm. The tenth wire netting features a leg length of approximately 65 mm.

Starting from a start of the press path, the spring characteristic curve 56j has a first partial characteristic curve 60j, extending approximately linearly and having a first gradient. The first partial characteristic curve 60j is followed by an approximately linearly extending second partial characteristic curve 62j with a second gradient which is greater than the first gradient. In a transition region 68j between the first partial characteristic curve 60j and the second partial characteristic curve 62j, the spring characteristic curve 56j has a kink 70j.

The second partial characteristic curve 62j is followed by a convexly curved third partial characteristic curve 64j. A transition between the second partial characteristic curve 62j and the third partial characteristic curve 64j is free of a kink.

REFERENCE NUMERALS 10 wire netting
12 helix
14 helix
16 longitudinal element
18 wire
20 leg
22 leg
24 bending region
26 gradient angle
28 longitudinal direction
30 gradient angle
32 bending region
34 bending zone
36 transition zone
38 transition zone
40 bending cylinder
42 test piece
44 transverse extension
46 test piece
48 plate
50 plate
52 press path
54 frontal direction
56 spring characteristic curve
58 press path-force diagram
60 partial characteristic curve curve
62 partial characteristic curve curve
64 partial characteristic curve curve
66 press path value range
68 transition zone
70 bend
72 press path value range
74 bending device
76 helix blank
78 bending unit
80 bending mandrel
82 bending table
84 feed unit
86 feed axis
88 feed direction
90 geometry-adjusting unit
92 transverse stroke unit
94 main extension direction
96 abutment unit
98 abutment element
100 abutment surface
102 pivot axis
104 holding unit
106 holding element
108 pivot axis 109 longitudinal axis
110 longitudinal axis
112 main extension direction
114 longitudinal axis
116 transition point
118 intersection angle
120 bending test device
122 clamping jaw
124 clamping jaw
126 bending cylinder
128 bending lever
130 driver
132 driver
133 bending distance
134 pressing device
136 press path axis
138 force axis
140 bending space
142 circulation direction
144 longitudinal axis
146 orientation element
148 conveying element
150 guiding table
152 guiding roll
154 guiding roll
156 transverse stroke direction
158 coupling element
160 transverse stroke
162 coupling element
164 belt
166 bending region
168 circular path
170 support pin
172 slotted link
174 slotted link
176 method step
178 method step
180 method step

The invention claimed is:

1. A wire netting comprising:
a plurality of helices which are braided with one another and at least one of which is manufactured of at least one single wire, a wire bundle, a wire strand, a wire rope, and/or another longitudinal element, which are each formed from at least one wire, in particular made of a high-tensile steel, wherein
the wire is bendable in a reverse bend test in opposite directions, by at least 90° respectively, about at least one bending cylinder having a diameter of maximally 2 d, at least M times without breaking, wherein M may be determined (by rounding down if applicable) to be $C \cdot R^{-0.5} \cdot d^{-0.5}$ and wherein a diameter d of the wire is given in mm, R is a tensile strength of the wire in N mm$^{-2}$ and C is a factor of at least 400 N$^{0.5}$ mm$^{0.5}$.

2. The wire netting according to claim 1, wherein the wire has a tensile strength of at least 800 N mm$^{-2}$.

3. The wire netting according to claim 1, wherein a helix of each of the plurality of helices comprises at least one first leg, at least one second leg and at least one bending region connecting the first leg and the second leg to one another.

4. The wire netting according to claim 3, wherein the first leg and/or the second leg at least section-wise follows a straight contour.

5. The wire netting according to claim 3, wherein the first leg extends at least section-wise in a first plane and the second leg extends at least section-wise in a second plane that is parallel to the first plane.

6. The wire netting according to claim 3, wherein, in a transverse view in parallel to a main extension plane of the helix and perpendicularly to a longitudinal direction of the helix, the bending region at least section-wise follows an at least approximately straight course.

7. The wire netting according to claim 1, wherein, in the transverse view, a helix of each of the plurality of helices follows at least section-wise a stepped course.

8. A method for an identification of a suitable wire, in particular a wire made of a high-tensile steel, and for manufacture of a wire netting with a plurality of helices which are braided with one another, wherein at least one of the helices is to be manufactured of at least one single wire, a wire bundle, a wire strand, a wire rope and/or another longitudinal element with the suitable wire, comprising:
performing a reverse bend test in which a test piece of the wire is bended in opposite directions, by at least 90° respectively, about at least one bending cylinder having a diameter of maximally 2 d, at least M times without breaking, wherein M may be determined (by rounding down if applicable) to be $C \cdot R^{-0.5} \cdot d^{-0.5}$, and wherein a diameter d of the wire is given in mm, R is a tensile strength of the wire in N mm$^{-2}$ and C is a factor of at least 400 N$^{0.5}$ mm$^{0.5}$; and
identifying the wire as suitable in response to the test piece of wire not breaking in the reverse bend test.

9. The method according to claim 8, further comprising forming a plurality of helices which are braided with one another from a wire, in particular a wire made of a high-tensile steel, that is identified as suitable for manufacturing and wherein at least one helix is manufactured of at least one single wire, a wire bundle, a wire strand, a wire rope and/or another longitudinal element with the identified wire by bending.

* * * * *

UNITED STATES PATENT AND TRADEMARK OFFICE
CERTIFICATE OF CORRECTION

PATENT NO. : 10,549,335 B2
APPLICATION NO. : 16/475868
DATED : February 4, 2020
INVENTOR(S) : Corinna Wendeler-Goeggelmann It is certified that error appears in the above-identified patent and that said Letters Patent is hereby corrected as shown below:

On the Title Page

Item (57), Line 13, change "$mm^{0.5}$" to --$mm^{-0.5}$--.

In the Specification

Column 3, Line 54, change "$mm^{0.5}$" to --$mm^{-0.5}$--.

Column 4, Line 19, change "$mm^{0.5}$" to --$mm^{-0.5}$--.

Column 13, Line 58, change "$mm^{0.5}$" to --$mm^{-0.5}$--.

Column 13, Line 61, change "$mm^{0.5}$ or no less than 750 $N^{0.5}$ $mm^{0.5}$" to --$mm^{-0.5}$ or no less than 750 $N^{0.5}$ $mm^{-0.5}$--.

Column 13, Line 62, change "$mm^{0.5}$ or no less than 1500 $N^{0.5}$ $mm^{0.5}$" to --$mm^{-0.5}$ or no less than 750 $N^{0.5}$ $mm^{-0.5}$--.

Column 24, Line 6, change "$mm^{0.5}$" to --$mm^{-0.5}$--.

Column 24, Line 14, change "$mm^{0.5}$" to --$mm^{-0.5}$--.

Column 24, Line 15, change "$mm^{0.5}$ or 1000 $N^{0.5}$ $mm^{0.5}$ or 2000 $N^{0.5}$ $mm^{0.5}$" to --$mm^{-0.5}$ or 1000 $N^{0.5}$ $mm^{-0.5}$ or 2000 $N^{0.5}$ $mm^{-0.5}$--.

Column 24, Line 19, change "$mm^{0.5}$" to --$mm^{-0.5}$--.

Signed and Sealed this
Twenty-first Day of April, 2020

Andrei Iancu
*Director of the United States Patent and Trademark Office*

In the Claims

Column 36, Line 3, change "mm$^{0.5}$" to --mm$^{-0.5}$--.

Column 36, Line 40, change "mm$^{0.5}$" to --mm$^{-0.5}$--.